(12) United States Patent
Nouadje et al.

(10) Patent No.: US 12,306,183 B2
(45) Date of Patent: May 20, 2025

(54) IMMUNOFIXATION ELECTROPHORESIS METHOD WITH TARGET COMPONENT ON-GEL IMMUNODISPLACEMENT

(71) Applicant: SEBIA, Lisses (FR)

(72) Inventors: Georges Nouadje, Bondoufle (FR); Thierry Ligneel, Bouray sur Juine (FR)

(73) Assignee: SEBIA, Lisses (FR)

( * ) Notice: Subject to any disclaimer, the term of this patent is extended or adjusted under 35 U.S.C. 154(b) by 0 days.

(21) Appl. No.: 16/320,521

(22) PCT Filed: Jul. 27, 2017

(86) PCT No.: PCT/EP2017/069077
§ 371 (c)(1),
(2) Date: Jan. 25, 2019

(87) PCT Pub. No.: WO2018/019961
PCT Pub. Date: Feb. 1, 2018

(65) Prior Publication Data
US 2019/0242891 A1 Aug. 8, 2019

(30) Foreign Application Priority Data
Jul. 27, 2016 (EP) .................................... 16305975

(51) Int. Cl.
| | | |
|---|---|---|
| G01N 33/561 | (2006.01) | |
| G01N 33/563 | (2006.01) | |
| G01N 33/68 | (2006.01) | |

(52) U.S. Cl.
CPC ......... *G01N 33/561* (2013.01); *G01N 33/563* (2013.01); *G01N 33/6857* (2013.01)

(58) Field of Classification Search
None
See application file for complete search history.

(56) References Cited

U.S. PATENT DOCUMENTS

| | | | |
|---|---|---|---|
| 5,567,282 | A | 10/1996 | Wang et al. |
| 8,609,435 | B2 | 12/2013 | Robert et al. |
| 8,859,211 | B2 | 10/2014 | Chaffey et al. |
| 2005/0164302 | A1 * | 7/2005 | Robert ............... G01N 33/6854 435/7.1 |
| 2010/0113752 | A1 * | 5/2010 | Chaffey ............... G01N 33/561 530/391.1 |

FOREIGN PATENT DOCUMENTS

| | | | | |
|---|---|---|---|---|
| CA | 02645622 | * | 10/2007 | ............... B01L 3/00 |
| EP | 2184606 A1 | * | 5/2010 | ............ G01N 33/561 |
| WO | WO 95/20160 | * | 7/1995 | ............. G01N 35/561 |

OTHER PUBLICATIONS

Litwin et al., Comparison of Capillary Zone and Immunosubtraction With Agarose Gel and Immunofixation Electrophoresis for Detecting and Identifying Monoclonal Gammopathies, Am J Clin Pathol 1999;112:411-417. (Year: 1999).*
Bossyt et al., Serum protein electrophoresis and immunofixation by a semiautomated electrophoresis system, Clinical Chemistry, vol. 44, Issue 5, May 1, 1998, pp. 944-994 (Year: 1998).*
Guancial et al., heraputic Monoclonal Antibody Interference In Immunofixation Electrophoresis, 116, 21, 2010, 4996. (Year: 2010).*
Zhu et al., "Protein separation by capillary gel electrophoresis: A review." Analytica Chimica Acta 709 (2012) 21-31.*
Li et al., "Clinical Analysis by Microchip Capillary Electrophoresis", Clinical Chemistry 52:1 37-45 (2006).*
International Search Report, mailed Oct. 26, 2017, from corresponding International Application No. PCT/EP2017/069077.
European Search Report, mailed Jan. 31, 2017, from corresponding EP Application No. 16305975.1-1408.
Alper et al., "Immunofixation Electrophoresis: A Technique for the Study of Protein Polymorphism", Vox Sanguinis, vol. 17, 1969, pp. 445-452.
Carter, "Potent antibody therapeutics by design", Nature Reviews: Immunology, vol. 6, May 2006, pp. 343-357.
Cawley et al., "Immunofixation Electrophoretic Techniques Applied to Identification of Proteins in Serum and Cerebrospinal Fluid", Clinical Chemistry, vol. 22, No. 8, 1976, pp. 1262-1268.
Cejka et al., "IgD Myeloma Protein with 'Unreactive' Light Chain Determinants", Clinical Chemistry, vol. 25, No. 8, 1979, pp. 1495-1498.
Durie et al., "International uniform response criteria for multiple myeloma", Leukemia, vol. 20, 2006, pp. 1467-1473.
Kirkwood et al., "Immunotherapy of Cancer in 2012", CA Cancer J Clin., vol. 62, No. 5, Sep. 2012, pp. 309-335.
Kola et al., "Can the pharmaceutical industry reduce attrition rates?", Nature Reviews: Drug Discovery, vol. 3, Aug. 2004, pp. 711-715.
Kubota et al., "Engineered therapeutic antibodies with improve deffector functions", Cancer Science, vol. 100, No. 9, Sep. 2009, pp. 1566-1572.
McCudden et al., "Interference of Monoclonal Antibody Therapies with Serum Protein Electrophoresis Tests", Clinical Chemistry, vol. 56, No. 12, 2010, pp. 1897-1899.
McCudden et al., "Monitoring multiple myeloma patients treated with daratumumab: teasing out monoclonal antibody interference", Clin. Chem. Lab Med., vol. 54, No. 6, 2016, pp. 1095-1104.

(Continued)

*Primary Examiner* — Ann Montgomery
(74) *Attorney, Agent, or Firm* — Arrigo, Lee, Guttman & Mouta-Bellum LLP

(57) ABSTRACT

Disclosed is a method for analyzing biological samples by immunofixation electrophoresis which involves immunodisplacement of target component(s) that may be present in the assayed biological sample, the target component(s) amounting to interfering component(s) when interpretation of the immunofixation results is considered. The immunodisplacement is carried out on an electrophoretic support that is preferably a gel, as defined herein. Accordingly, the invention provides IFE using an antibody or antibodies which is(are) modified (modified antibody) to bear additional negative electric charges, the modified antibody(ies) having antigenic specificity for a predetermined target immunoglobulin.

29 Claims, 11 Drawing Sheets

(56) References Cited

OTHER PUBLICATIONS

Pavlou et al., "The therapeutic antibodies market to 2008", European Journal of Pharmaceutics and Biopharmaceutics, vol. 59, 2005, pp. 389-396.
Reichert et al., "Monoclonal antibody successes in the clinic", Nature Biotechnology, vol. 23, No. 9, Sep. 2005, pp. 1073-1078.
Reichert, "Antibodies to watch in 2010", mAbs., vol. 2, Issue 1, Jan. 2010, pp. 84-100.
Ritchie et al., "Immunofixation. II: Application to typing of alpha1-antitrypsin at acid pH", Clinical Chemistry, vol. 22, No. 10, 1976, pp. 1735-1737.
Ritchie et al., "Immunofixation. I. General Principles and Application to Agarose Gel Electrophoresis", Clinical Chemistry, vol. 22, No. 4, 1976, pp. 497-499.
Ritchie et al., "Immunofixation. III. Application to the Study of Monoclonal Proteins", Clinical Chemistry, vol. 22, No. 12, 1976, pp. 1982-1985.
Rosman et al., "Biologic therapy for autoimmune diseases: an update", BMC Medicine, vol. 11, No. 88, 2013, pp. 1-12.
Ruinemans-Koerts et al., "Interference of therapeutic monoclonal immunoglobulins in the investigation of M-proteins", Clin. Chem. Lab. Med., vol. 52, No. 11, 2014, pp. e235-e237.
Su et al., "Severe Isopropanolemia Without Acetonemia: Contamination of Specimens During Venipuncture?", Clinical Chemistry, vol. 41, No. 1, 1995, pp. 121-123.

\* cited by examiner

IMMUNOFIXATION ELECTROPHORESIS METHOD WITH TARGET COMPONENT ON-GEL IMMUNODISPLACEMENT

FIELD OF THE INVENTION

The invention relates to the field of analysis of biological samples by immunofixation electrophoresis (IFE).

The invention especially relates to a method for analyzing biological samples by immunofixation electrophoresis which involves immunodisplacement of target component(s) that may be present in the assayed biological sample, said target component(s) amounting to interfering component(s) when interpretation of the immunofixation results is considered. The immunodisplacement is carried out on an electrophoretic support that is preferably a gel, as defined herein.

In this respect, the invention relates to an improved immunofixation electrophoresis method that can profitably be applied in the context of diagnostic protocols, when investigation and/or typing in biological samples of proteins that can witness monoclonal disorders, also known as monoclonal gammopathies is sought. The improvement brought by the present invention will be immediately apparent by comparison to the results that can be obtained using a classical immunofixation electrophoresis method when assaying a biological sample encompassing interfering component(s) as defined herein, where the visual representation of the results, using a classical method, renders them difficulty interpretable.

The invention is also of particular interest for the monitoring of patients following a therapy involving administration of therapeutic monoclonal antibodies. In particular, the methods described herein enable a complete elimination of the administered therapeutic monoclonal antibodies from results visualization, especially when said administered therapeutic monoclonal antibodies can be confused with endogenous immunoglobulins.

The invention also relates to a kit suitable for implementing the method(s) described herein.

BACKGROUND OF THE INVENTION

Serum protein electrophoresis (SPE) and Immunofixation electrophoresis (IFE) are methods broadly used in clinical laboratories for the detection, identification, and follow-up of the progression of immunoglobulins involved in monoclonal gammopathies.

Several illnesses can present with a monoclonal gammopathy, such as Monoclonal gammopathy of undetermined significance (MGUS), but also Multiple myeloma, AIDS, Chronic lymphocytic leukemia, Non-Hodgkin Lymphoma, particularly Splenic marginal zone lymphoma and Lymphoplasmocytic lymphoma, Hepatitis C, Connective tissue disease such as lupus, Immunosuppression following organ transplantation, Waldenstrom macroglobulinemia, Guillain-Barre syndrome or Tempi syndrome.

Immunofixation electrophoresis (IFE), i.e., "classical" IFE, is a well-established method for detecting and typing certain proteins, especially monoclonal antibodies or immunoglobulins in biological samples. Assayed biological samples are usually serum, urine and cerebrospinal fluid. IFE is a two-stage procedure combining protein electrophoresis as a first step and immunofixation as a second step. That technique is widely used as routine analysis carried out, in particular in clinical analysis laboratories, for analyzing biological samples with a view to typing the immunoglobulins (also termed monoclonal proteins or monoclonal components/antibodies/immunoglobulins herein) they contain. That technique, which combines electrophoresis with the formation of precipitates on the electrophoresis gel, has been known for a long time and is in particular described by Alper C A and Johnson A M Vox. Sang. 17: 445 (1969), Cawley L P et al., Clin. Chem. 22: 1262 (1976), Ritchie R F and Smith R Clin. Chem. 22: 497, 1735, 1982 (1976). It allows the identification of anomalies in different biological samples, in particular in biological liquids, for example serum, urine or cerebrospinal fluid.

In the first step of IFE, electrophoresis of the protein content of a biological sample is performed on an electrophoretic support (usually a gel) under an applied electric field. This allows protein fraction(s) separation (resolution) in the form of an electrophoretic profile.

Gel protein electrophoresis exploits the fact that proteins in the gel have an intrinsic electrical charge. When applying an electric field, the intrinsic charge of a given protein imparts an electrophoretic mobility to said protein and thus permits its migration in the gel toward an electrode having a charge opposite to the charge of the protein. As a biological sample contains several protein types, proteins having lower electrophoretic mobility will move slower than those with higher electrophoretic mobility and hence separation of the proteins of the biological sample from one another can be achieved.

In the second step of IFE, immunofixation is performed to permit the detection and typing of the monoclonal antibodies or immunoglobulins that may be present in the assayed sample. To this end, several aliquots of the same biological sample are deposited in parallel on agarose gel. After the electrophoresis of the first step, each electrophoresed track is incubated with a type of antibody that is specific to the types of immunoglobulins being investigated (IgG, IgA, IgM, kappa and lambda, and possibly free kappa, free lambda, IgD and IgE), leading to the formation of immunocomplexes between the immunoglobulins in the sample and the antibodies. After washing the gel to eliminate non-precipitated proteins, a staining step can reveal the position of the immunocomplexes: in the absence of monoclonal proteins, only a diffuse stained background appears (corresponding to a multitude of monoclonal antibodies constituting the "polyclonal background"); in the presence of monoclonal proteins, stained bands are revealed in specific regions of the gel. The use of a reference track on which no antiserum is applied, enables the typing of each monoclonal band that is visible on the gel, by comparison with the reference track Immunoglobulins are generally formed from heavy chains (2 heavy chains) and light chains (2 light chains). Five heavy chain isotypes (M, G, A, D, E—isotypic classes) and two light chain isotypes (kappa and lambda—isotypic types) have been identified in that four-chain structure. Depending on the diseases of the investigated patients, monoclonal proteins that can be identified are of a different nature, constituted either by an intact antibody molecule, or by a fragment of antibody. Thus, heavy chains or light chains can be produced alone. This is the case, for example, with Bence Jones proteins secreted in the urine of patients with myelomas, which are in the form of light chains alone. The isotypes that are to be determined for the immunoglobulins can be characterized as a function of the nature of their heavy chains and/or as a function of the nature of their light chains.

Thus, according to IFE procedures known in the art, i.e., "classical" IFE, a fixative solution (for electrophoresed reference track, termed ELP herein) and antisera comprising capture antibodies which are specific for different immunoglobulin classes and types (e.g., IgG, IgA, IgM, IgK, IgL, IgKfree, IgLfree) can be applied to determined tracks of the gel. The gel, fixative solution and these different antisera (capture antibodies) are incubated during a time during which immune complexes are formed between the specific immunoglobulin(s) and the capture antibodies. The locations of such immune complexes on the gel can then visualized by staining the gel. As a result, the presence of a specific band is generally indicative of the presence of a monoclonal protein corresponding to a particular immunoglobulin class and type. A "monoclonal protein" is characterized by heavy chains of a single isotypic class (and possibly subclass, although conventional IFE does not analyze this parameter) and by light chains of a single isotypic type.

State of the art apparatuses perfoming IFE, i.e., "classical" IFE, are known. For example, the commercially available Hydrasys® electrophoresis system (SEBIA) is a semi-automated multi-parameter instrument enabling carrying out IFE from start-to finish: application of samples onto the gel, migration, incubation of the gel with antisera (capture antibodies), staining/destaining and final-stage drying can be performed in a semi-automated manner following the instructions of the manufacturer. The Hydrasys® electrophoresis system possesses a carrier applicator for applying samples onto the gel, which include 13 different positions for sample application onto the gel. Depending on the selected program, the system can simultaneously process 1, 2, 4 or 9 immunofixation samples (1). Implementation of the method of the invention is described in the Examples section below using the Hydrasys® electrophoresis system. However, the skilled person will readily rely on the principle described herein for implementing the methods described herein on other conventional apparatuses designed for carrying out IFE procedures, electrophoresis and immunofixation steps remaining the same.

Apart from Serum protein electrophoresis (SPE) and classical Immunofixation electrophoresis (IFE), Capillary Electrophoresis (CE) is also used for electrophoretic analysis of the immunoglobulins contained in a biological sample. A particular adaptation of CE relying on an immunodisplacement step, is currently used for identifying monoclonal proteins which may be present in an analysed biological sample. Capillary Electrophoresis Immunodisplacement may use a chemically modified antibody that despite such modification retains its ability to bind monoclonal proteins. This chemical modification provides additional negative charge to the antibodies to allow antibodies and their complexes to move out of the gamma zone, (14-15) or out of the serum protein pattern during the electrophoretic migration (16).

For this purpose and in the context of Immunodisplacement CE, it is observed that the sample is necessarily pre-incubated with a specific modified antiserum (antibody), before subjecting the resulting mixture to capillary electrophoresis process. Disappearance or not of a peak from gamma zone during the migration with this specific modified antiserum allows, in simple cases, the classification and typing of the sample. Of note, resolving an interpretation difficulty or a therapeutic monoclonal interferent in the context of an Immunodisplacement CE assay necessarily requires performance of several complementary tests, and a modification of the pre-analytical phase, which may render the setting and/or results interpretation even more difficult. In any event however, interpretation of the results that can be obtained through CE, can remain difficult, even when using Immunodisplacement CE, in addition to the fact that sensitivity of Immunodisplacement CE remains lower than the sensitivity of conventional IFE. Also, conventional IFE remains the gold standard for immunoglobulins typing and follow-up of patients presenting multiple myeloma, although subject to other problems, as discussed below.

Although the interpretation of IFE results can be seen as a very qualitative exercise, subject to the experience and skills of the practitioner, the interpretation of the results of conventional IFE experiments is considered easier than that of other techniques (e.g., SPE or CE) for the skilled in the art, except in certain situations. In fact, current (classical) IFE methods do not always avoid the presence of confusing patterns. For example, in the presence of two or more monoclonal components in the analysed sample, for example as a result of the proliferation of several clones of B-cells in a patient, several monoclonal bands should be revealed by immunofixation. When a biclonal gammopathy is present, two bands of heavy chain (identical or different) and two bands of light chains (identical or different) should be seen by immunofixation. However, such biclonal bands can co-migrate and thus render the interpretation difficult. When an oligoclonal gammopathy is present, multiple, possibly weak bands of one or more types of heavy chains and one or two types of light chains should be seen. However, detection of an oligoclonal gammopathy in the presence of a significant polyclonal background may be dubious. Similarly, in the presence of a polyclonal background, especially when the analyzed sample is diluted to minimize the interference of said polyclonal background on antisera (capture antibodies) tracks, the monoclonal protein that the analyzed sample may contain may also be diluted so as to render it invisible in the polyclonal background. In this case, the possibility of the presence of monoclonal protein cannot be excluded.

From the above, it can be seen that in several cases interpretation of the results of the IFE performed using current conventional methods can be difficult. Generally, the presence of so-called interfering protein(s) or component(s), also termed "interferent(s)" herein, that can co-migrate on an IFE gel renders the interpretation more difficult. This problem has no solution in the art.

In addition, to date, monoclonal antibody therapeutics are increasingly being used in numerous medical disciplines including allergy immunology, gastroenterology, haematology, oncology, rheumatology, and dermatology and organ transplantation (2-9). In this context, drug interference on serum IFE performed on samples collected from treated patients or spiked serum samples has been described with a number of therapeutic monoclonal antibodies (11-12).

On the other hand, the presence of monoclonal antibody therapeutics may also lead clinicians to falsely suspect conditions such as monoclonal gammopathy of undetermined significance (MGUS). As clinical laboratories are rarely provided with extensive patient history, it is likely that faint monoclonal components unknowingly due to monoclonal antibody therapeutics are being reported (13).

Here again, presence of exogenous interfering protein(s) or component(s) (interferent(s)) under the form of a monoclonal antibody administered to a patient, which can co-migrate with endogeneous monoclonal protein(s) or component(s) when performing an IFE on said patient's sample, renders the interpretation more difficult.

It is also known from (20) (McCudden C et al., Clin Chem Lab Med 2016 Jun. 1; 54(6):1095-104, Monitoring multiple myeloma patients treated with daratumumab: teasing out monoclonal antibody interference) a so-called DIRA method that has been implemented to minimize the impact of daratumumab as an interferent. The assayed sample has been pre-incubated with a non-modified anti-daratumumab antibody, and the resulting incubated mixture deposited on a gel, further subjected to migration and immunofixation. Daratumumab as an interferent remains in the gamma zone, and numerous supplementary tracks are mandatory to even demonstrate that the displaced band actually corresponds to daratumumab. It is observed that the daratumumab/anti-daratumumab complex is found, using said DIRA technique, in the gamma zone: a risk therefore remains with respect of a migration of said complex with a monoclonal band. In addition, the sample is diluted and pre-incubated with anti-daratumumab anitobdy before on gel deposit of the pre-incubated sample: such a procedure requires provision and consumption of an important quantity and volume of anti-daratumumab antibody, which hinders the costs associated with such a medical procedure.

There is therefore a need to overcome part or all of these problems, as disclosed herein, when analysis of samples by IFE, which are susceptible to contain or contain exogenous or endogenous interfering component(s) is performed. Said exogenous or endogenous interfering component(s) are components that can render the interpretation of the IFE more difficult, as explained above. The interfering component(s) may be interfering exogenous or endogenous antibody(ies) or immunoglobulins(s), such as therapeutic monoclonal antibody(ies) or endogenous immunoglobulins(s), including endogenous monoclonal antibody(ies) or polyclonal antiserum(a) or component(s) thereof contained in the sample patient that is analyzed.

The presence of such interfering component(s) in a sample analyzed by IFE can have the consequence to lead to an erroneous or dubious clinical interpretation of the IFE, or make it impossible.

The present invention proposes a solution to these problems. In this respect, the invention relates to an (improved) method of analysis by IFE enabling superior interpretation facility of IFE results, which can therefore profitably be applied in diagnostic protocols, when investigation and/or typing in biological samples of proteins that can witness monoclonal disorders, also known as monoclonal gammopathies is sought, in a cost-effective way. The invention is also of particular interest for the monitoring of patients following a therapy involving administration of therapeutic monoclonal antibodies.

It is an advantage of the present invention that the method discussed herein, in fact amounts to a method that can be performed without adding much steps to a conventional immunofixation electrophoresis (IFE) procedure. In fact, only one step is added, which corresponds to the deposit of modified antibodies, as discussed herein, on the gel. There is accordingly no other modification of classical IFE protocol, in order to achieved very advantageous results, e.g., mitigating immunoglobulin interferences and resolving interpretation difficulties usually observed with classical IFE when analyzing biological samples.

Since the methods described herein extensively clarify the result of IFE for interpretation purpose, the methods described herein can also be defined as methods for improving immunofixation electrophoresis data exploitation when analyzing biological samples comprising or susceptible to comprise target component(s) amounting to interfering component(s) when interpretation of the immunofixation results is considered, by contrast to known (classical) immunofixation electrophoresis methods.

In other words, it will be appreciated that the present invention is a direct technique, with no reagent pre-treatment and no pre-analytical step, that is readily compatible with state of the art IFE protocols in the sense the technique is easy to use and easy to implement without numerous further steps (unchanged apparatus protocol), wherein said method advantageously provides superior interpretation facility while ensuring effective and efficient clarification of an assayed sample containing interferent(s), wherein said method also optimizes the volume of necessary reagents, in a cost-effective way.

SUMMARY OF THE INVENTION

The present invention thus concerns a method for immunofixation electrophoresis (IFE) analysis of a biological sample comprising one or more protein(s), in particular for IFE analysis of monoclonal component(s) that may be present in said biological sample, comprising the steps of:
a. depositing at least one aliquot portion of the biological sample on a deposit area of an electrophoretic gel plate, said sample deposit area being at a position of the gel plate enabling electrophoretic migration of the protein content of the deposited sample towards the anodic side of the gel plate, and
b. depositing at least one antibody which is modified (modified antibody) to bear additional negative electric charges, said modified antibody having antigenic specificity for a predetermined target immunoglobulin or fragment thereof that may be present in the biological sample and having the capacity/capability to form an immunocomplex, especially a soluble immunocomplex, with said predetermined target immunoglobulin or fragment thereof, wherein the at least one modified antibody is deposited on a deposit area of the electrophoretic gel plate that coincides with the sample deposit area of step a. or is separated from the deposit area of step a., being on the same track but at a position that is more cathodic with respect to the position of the sample deposit area of step a., in particular between the cathodic extremity of the gel plate and the sample deposit area of step a.,
wherein steps a. and b. can be performed in any order or at the same time when the modified antibody deposit area and the sample deposit area are separated, or in any order when the modified antibody deposit area and the sample deposit area coincide, and
c. electrophoresing the gel plate to obtain a protein separation profile of the biological sample deposited in step a., the at least one modified antibody deposited in step b. displacing specifically the predetermined target immunoglobulin or fragment thereof that may be present in the biological sample outside the gamma zone and/or protein profile during the electrophoretic migration, and
d. applying at least one capture antibody on appropriate zone(s) of the electrophoresed gel plate, wherein said capture antibody has specificity for a particular (determined) antibody isotype, or has specificity for the target immunoglobulin or fragment thereof, or has specificity for a particular (determined) antibody isotype and/or target immunoglobulin or fragment thereof as found in an immunocomplex between the target immunoglobulin or fragment thereof and the at least one modified antibody, and permitting its reaction to enable the formation of precipitated and/or detectable immunocomplexes, and e. optionally, staining the immunocomplexes formed in step c. and optionally step d.

The target immunoglobulin or fragment thereof recognized and bound by the modified antibody in the method of the invention may be an immunoglobulin or fragment thereof associated with a pathological condition such as pathological monoclonal components, or an immunoglobulin or fragment thereof that may interfere with the proper analysis of the sample thereby giving rise to confusing IFE profiles. It will be understood that the predetermined target immunoglobulin or fragment thereof defined herein corresponds to an exogenous or endogenous interfering component that can be found in the assayed biological sample. An exogenous or endogenous interfering component can be an exogenous or endogenous antibody or immunoglobulin, such as a therapeutic monoclonal antibody, or endogenous immunoglobulins, including endogenous monoclonal antibody or polyclonal antiserum or component thereof. The invention is also applicable to the detection of mixtures of interfering components, as defined herein.

Presence of monoclonal component(s) in a biological sample is characteristic of an excessive production of one single type of immunoglobulin belonging to a class selected amongst IgG, IgA, IgM, IgD or IgE. Monoclonal component(s) arise from the proliferation of one specific clone of malignant or hyperstimulated B cells which in turn generates a homogenous population of monoclonal immunoglobulins.

By "monoclonal component(s)" it is therefore meant an immunoglobulin belonging to the above mentioned classes, or a fragment thereof, as defined by heavy and/or light chain immunoglobulin isotypes and produced by a single specific clone of B cells in association with a pathological context. As defined herein, monoclonal component(s) include free light chains (kappa and lambda). The IFE method described herein allows the analysis of the content in protein(s) of a biological sample, including or in addition to analysis of the monoclonal component(s) it may contain. The IFE method described herein also allows analysis of sample containing polyclonal antisera.

Conversely, a target immunoglobulin or fragment thereof as defined herein can have the same structural characteristics as "monoclonal component(s)" as defined herein.

Presence of therapeutic antibodies in a sample is normally associated with a medicinal treatment of a patient that may be unknown from the practitioner in charge of the IFE analysis.

It is provided that in accordance with the invention the target immunoglobulin or fragment thereof may be a plurality of distinct immunoglobulins or fragments thereof such as monoclonal components as defined herein.

Also, by reference to "at least one antibody which is modified to bear additional negative electric charges", and according to a particular embodiment, it is also meant a mixture of several antibodies having antigenic specificity for multiple and respectively distinct predetermined target immunoglobulin(s) or fragment(s) thereof as defined herein.

In general terms, the present invention provides a process of on-gel immunodisplacement that is used in conjunction with immunofixation electrophoresis, with the view to displacing specifically at least one predetermined target, including interfering, immunoglobulin or fragment thereof out of a zone of interest, especially out of the gamma zone, on an electrophoretic support that is a gel such as an agarose gel, by using at least one modified antibody specific for at least one predetermined target immunoglobulin or fragment thereof.

By "zone of interest" in the expression "out of a zone of interest", reference is made to the zone(s) commonly identified on an electrophoretic gel plate, which is an IFE gel plate, by the skilled person. The present invention seeks removal of interfering target immunoglobulin(s) or fragment(s) thereof (also termed interferent(s) herein) from a zone of interest that can correspond to the "gamma" zone, or also, according to other particular embodiments, a zone ranging from the gamma zone (that is closer to the cathodic side of the electrophoretic gel plate) to the beta or alpha, including alpha1 and/or alpha2, zone(s) of the electrophoretic gel plate. According to a particular embodiment, the displacement is achieved outside the gamma zone during the electrophoretic migration phase. According to another particular embodiment, the displacement is achieved outside the alpha zone, in particular outside the alpha1, or outside the alpha2 zone. According to another particular embodiment, the displacement is achieved outside the protein profile of the sample taken as a whole.

It will be understood that the expressions used herein to qualify the zone(s) commonly identified on an electrophoretic gel plate by the skilled person are conventional in the art. Especially, the skilled person can readily define the extent of a so-called "gamma", "alpha", or "beta" zone (or region). Such zones or regions are those visualized on an electrophoretic profile when presence and/or characterization of immunoglobulins is/are sought using electrophoretic migration. These zones or regions are those where migrating alpha1, alpha2, beta and gamma globulins can be found upon completion of electrophoretic process. The common knowledge of the skilled person readily enables him/her to determine and identify the boundaries and extent of such zones or regions when observing a globulin electrophoretic migration profile. Such terms and expression are commonly at the basis of said technique in the art. Reference is for example made to the booklet "Serum protein electrophoresis immunofixation—Illustrated interpretations", Didier Le Carrer, SEBIA, 2005, ISBN 2-9521005-6-X.

The present invention can therefore be seen as an improvement for immunofixation electrophoresis of samples containing exogenous interfering component(s) (such as therapeutic monoclonal antibodies) or endogeneous interfering component(s), which are the so-called predetermined target (interfering) immunoglobulins or fragments thereof.

According to this aspect and outstanding advantage, the present invention is relevant for the analysis of certain biological samples that give confusing immunofixation electrophoresis patterns, such as biologicals samples of patients having biclonal (two identical bands of heavy chain and two different bands of light chains located at the same position on the electrophoresis pattern) or oligoclonal gammopathies, or samples of patients in which the presence of an immunoglobulin heavy chain is detected without corresponding light chain.

It can appreciated that the methods described herein in fact amount to an in situ interference displacement IFE methods, i.e., in situ meaning that the displacement is carried out only after deposit, on a gel, of the interferent(s) putatively contained in a sample and the complexing agent(s) enabling interferent(s) displacement, and further interaction, in situ within the gel, between said putative interferent(s) and said complexing agent(s), which may be subsequent to the application of an electric field. Differently said, the interferent(s) putatively contained in a sample and the complexing agent(s) enabling interferent(s) displacement to be carried out, can only interact between each other after their deposition on the gel. According to a particular embodiment, said interferent(s) putatively contained in a sample and the complexing agent(s) enabling interferent(s) displacement to be carried out, can only interact between each other after their deposition on the gel and after application of an electric field. In particular, the method does not require a sample pre-incubation step with an antibody. It is an advantage of the invention that the methods described herein enable both a lower reagents consumption, and improved results interpretation facility. In addition, the "interferent(s)" is/are shifted outside the gamma zone, which is correlated with a lower risk of co-migration of said interferent(s), for example endogenous M-proteins or monoclonal FLCs, especially when such entities are found in excess in the analyzed tracks. According to a particular embodiment, the immunofixation procedure following the electrophoresis in presence of a modified antibody uses common anti-immunoglobulins sera (capture antibody(ies)) for typing purposes. Anti-immunoglobulins sera (capture antibody(ies)) can be of human or animal origin.

According to a preferred embodiment, capture antibody (ies) are of animal origin. According to a particular embodiment, capture antibody(ies) can be rabbit antibody(ies). Said capture antibody(ies)) can recognize a particular antibody isotype in order to reveal its presence. Said capture antibody (ies)) can also recognize the target immunoglobulin or fragment thereof as defined herein (especially interfering immunoglobulin). According to another embodiment, said capture antibody(ies)) can also recognize a particular antibody isotype as found in an immunocomplex between the target immunoglobulin or fragment thereof (especially interfering immunoglobulin) and a modified antibody as defined herein.

According to a particular embodiment, capture antibody (ies)) recognize a soluble immunocomplex involving the target immunoglobulin or fragment thereof (especially interfering immunoglobulin) as defined herein. By "soluble immunocomplex", it is meant a complex that does not precipitate or is not found in a precipitated form in a medium consisting of an electrophoretic gel as defined herein, especially an electrophoretic gel used for carrying out the method of the invention.

The invention is based on the fact that a modified antibody loaded on the electrophoretic gel close to sample application area(s), migrates faster due to chemical modification providing it with additional negative electric charges with respect to the non-modified antibody, during the electrophoresis process, enabling it to bind specifically the predetermined target immunoglobulin or fragment thereof and shift it outside the gamma zone, or outside a zone of interest as defined herein.

The invention also relates to a kit suitable for carrying out a method of the invention, especially a kit containing a modified antibody solution against a predetermined target immunoglobulin or fragment thereof (exogenous or protein) and an additional sample loader.

Advantageously, such a kit is to be used in conjunction with available immunofixation protocols and/or kits, such as the IF programs and/or kits available for the Hydrasys® device without any change of protocol or program, apart the presence of an additional sample loader and modified antibody. According to a particular aspect, such a kit can further encompass mask(s) for applying modified antibody(ies) on a conventional (i.e., known or adapted) sample loader, in order to apply said modified antibody(ies) on appropriate lane(s) of the electrophoretic gel. Advantageously with respect to known immunofixation methods, the present invention does neither require any modification of biological sample pre-dilution(s) nor biological sample incubation with a modified antibody prior to the electrophoresis or the running of the (immunofixation) program on an instrument, nor biological sample incubation with a modified antibody prior to application of the reagents (assayed sample and modified antibodies) on the assay medium, as it is the case with known immunodisplacement capillary electrophoresis methods.

DETAILED DESCRIPTION

According to particular embodiments, the analyzed biological samples are selected amongst: serum, urine and cerebrospinal fluid samples.

All types of conventional electrophoretic gel types can be used.

According to a particular embodiment, the electrophoretic gel plate corresponds to a high resolution gel, such as an agarose gel, which shall improve the resolution in the gamma zone of the gel. Suitable agarose gels are known in the art. Common and suitable agarose can have a concentration of agarose from 0.5% to 2%. According to a particular embodiment, the concentration of agarose is 0.8%.

Other type of gels can however be used, including acrylamide gels.

According to a particular embodiment, the predetermined (interfering) immunoglobulin or fragment thereof is a therapeutic antibody, in particular a therapeutic recombinant monoclonal antibody.

Therapeutic recombinant monoclonal antibodies may be mouse-derived (the "-omabs"), humanized (the "-zumabs") or may be chimeric human-mouse antibodies (the "-ximabs") or human monoclonal antibodies (-umabs"). Therefore, they can appear as a visible monoclonal protein band in the electrophoresis pattern of patients receiving recombinant monoclonal antibody therapeutics.

Particularly and to date, humanized and human-mouse chimeric monoclonal antibodies can be seen when performing immunofixation and can wrongly be marked as monoclonal protein or can co-migrate with endogenous monoclonal proteins. In these cases, a follow-up testing with immunofixation electrophoresis method is not easy or impossible before the completion of the therapy. In the particular case of multiple myeloma, the international myeloma working group (IMWG) has established criteria for clinical response to the treatment, which include changes of monoclonal levels in serum by SPE and IFE (10). In IFE testing, for a patient to be classified as having complete response to the treatment using IMWG criteria, the serum must be negative for monoclonal protein(s), with no band appearing. Thus, drugs interferences can have a clinically important impact on the assessment of response to the treatment (11-12). Also, in the absence of provision of an extensive patient history to the practitioner performing an IFE, and since the presence of monoclonal antibody therapeutics may lead clinicians to falsely suspect conditions such as monoclonal gammopathy of undetermined significance (MGUS), it is likely that faint monoclonal components unknowingly due to monoclonal antibody therapeutics can be reported (13). The present invention overcomes these problems.

Monoclonal antibodies designed for therapeutic use and targeted in accordance with the invention usually belong to the IgG class. Therefore, according to a particular embodiment, the predetermined target immunoglobulin or fragment thereof is a therapeutic monoclonal antibody pertaining to IgG class. However, it will be understood that the present invention is readily applicable to all types of therapeutic monoclonal antibodies, without distinction of type or class, as disclosed herein, and include all known subclasses. Also, therapeutic monoclonal antibodies may encompass antibodies with other structures than that of naturally occurring antibodies. They can be human, humanized murine or chimeric antibodies, or variants thereof, especially chemically engineered variants or a vector monoclonal antibody, for example coupled to a drug. Are included herein within the definition of "therapeutic monoclonal antibody": whole (full) monoclonal antibodies, Fab fragments, F(ab')2 fragments, scFv (single-chain variable fragment), di-scFv (dimeric single-chain variable fragment), sdAb (single-domain antibody), bispecific monoclonal antibodies such as trifunctional antibody or chemically linked F(ab')2 fragments but also BiTE (bi-specific T-cell engager).

Since the "target immunoglobulin or fragment thereof" discussed herein can be readily found in any therapeutic monoclonal antibody, it is understood that the present invention is applicable to all available types of therapeutic monoclonal antibodies, without distinction.

Encompassed therapeutic monoclonal antibodies may be anti-cancer monoclonal antibodies, which may target malignant cells by several mechanisms. They can also be used in radioimmunotherapy, or in antibody-directed enzyme prodrug therapy (ADEPT), where they are linked to a drug-activating enzyme. onoclonal antibodies may be used in checkpoint therapy, where they are used to circumvent the defenses that tumors use to suppress the immune system. Monoclonal antibodies are also used for autoimmune diseases.

Therapeutic monoclonal antibodies may be specific for cell receptors, for cytokines such as IFN-α, interleukins, chemokines, interferons, or growth factors.

Examples of therapeutic monoclonal antibodies targets include alpha-4 (a4) integrin, an epitope of the RSV F protein, anti-IL-6R, CTLA-4, PD-1, CD11a, CD20, CD30, CD38, CD52, complement system protein C5, epidermal growth factor receptor, ErbB2, IL-12, IL-23, 1L-1β, IL-2Rα receptor (CD25), immunoglobulin E (IgE), inhibition of glycoprotein 11b/111a, inhibition of TNF-α signaling, inihibition of B-cell activating factor, integrin α4β7, RANK Ligand inhibitor, T cell CD3 Receptor, targets the programmed cell death 1 (PD-1) receptor, TNF-alpha inihibitor, vascular endothelial growth factor (VEGF), vascular endothelial growth factor A (VEGF-A).

According to a particular embodiment, the therapeutic monoclonal antibody is selected amongst: Adalimumab, Trastuzumab, Ofatumumab, Siltuximab, Rituximab, Bevacizumab, Infliximab, Cetuximab and Efalizumab, Natalizumab, Panitumumab, Tolicizumab,C lenoliximab, Etaracizumab, Visilizumab, Elotuzumab, Nimotuzumab, Ramicirumab, Elotuzumab, Daratumumab, Mapatumumab, Golimumab, Ustekinumab, Nivolumab, functionally equivalent antibodies, i.e., antibodies having the same antigenic target, or any mixture thereof.

According to another particular embodiment, the predetermined target immunoglobulin or fragment thereof is an endogeneous monoclonal immunoglobulin, or a fragment thereof.

According to another particular embodiment, the predetermined target immunoglobulin or fragment thereof is an endogeneous polyclonal antiserum (or a component of this polyclonal antiserum as found within said polyclonal antiserum).

When the predetermined target immunoglobulin or fragment thereof is an endogeneous immunoglobulin or fragment thereof, and according to a more particular embodiment, it can be selected amongst: IgG, IgA, IgM, IgD, IgE, kappa chain, lambda chain, free kappa chain and free lambda chain.

According to a more particular embodiment, predetermined target immunoglobulin or fragment thereof is a mixture of the above targets (and can be a so-called "polyclonal component/background").

For example, in the case of an oligoclonal profile where it is suspected that several bands have to be identified through IFE, along with a significant polyclonal background mainly in the G track, the interfering target is accordingly the significant polyclonal G background, which accordingly involves both lambda and kappa IgGs. It can be displaced by modified anti-IgLambda antibody and anti-IgKappa antibody. This enables to clarify the IgG track and helps to assess for instance the persistent monoclonal band that can also have been identified before a possible patient's treatment.

In this respect, it is observed that the methods of the invention disclosed in any embodiment herein actually enables to displace both the kappa and/or lambda components of a particular immunoglobulin isotype (such as the IgG isotype in the example above) within a single experiment (a polyclonal background is composed of the sum of kappa and lambda components), which enables an effective and efficient clarification of the results for interpretation purposes (in addition to reading facility). The interpretation is enabled, according to the present invention, at a glance, which was not possible using prior art methods. At the same time, the invention enables to immediately observing whether a weak band as found in a polyclonal background corresponds to a kappa or a lambda component. Of note, using Capillary Electrophoresis methods, it is not possible to dissociate kappa and lambda component of a particular immunoglobulin isotype within a single experiment. The running of several distinct capillaries would be required, which would also not necessarily facilitate interpretation, in addition to the multiple steps to be carried out.

In addition, several distinct therapeutic monoclonal antibodies can be found in the sample of a patient subjected to a multi-therapy.

Accordingly, the target immunoglobulin or fragment thereof can be of one or more than one type, or conversely the modified antibodies used (and respective capture antibodies used) can be one or more than one, i.e., two, three, four or more antibodies. Unless indicated differently, the technical elements described herein at the "singular" with respect to this point also apply at the "plural" form. The antibody to be modified may be an human monoclonal antibody or human polyclonal antisera depending on the target immunoglobulin or fragment thereof to be displaced. The antibody to be modified may be from human or from any animal host.

According to a particular embodiment, the antibody that is modified is a human or animal monoclonal antibody, or a human or animal polyclonal antiserum, in particular a monoclonal antibody or polyclonal antiserum specific for an immunoglobulin pertaining to an isotypic class selected amongst: IgG, IgA, IgM, IgD and IgE, or specific for an immunoglobulin pertaining to an isotypic type selected amongst: kappa and lambda, or specific for a free light chain selected amongst: free kappa and free lambda.

According to a particular aspect, the modified antibody has the structure of a whole (full) antibody. According to a particular embodiment, the modified antibody is an antibody raised against a therapeutic monoclonal antibody such as those disclosed herein and the modified antibody is prepared using antibodies against therapeutic antibodies provided by the manufacturer and modified for use in the method of the invention.

According to a particular embodiment, the modified antibody is modified to bear "additional" negative electric charges, and thereby possesses an increased intrinsic negative charge with respect to the same non-modified antibody of origin. By "additional" it is therefore meant that the amount of negative electrical charges on the antibody or the intrinsic negative charge of the antibody is increased with respect to the non-modified antibody of origin, taken in the same conditions. However, the modification carried out shall not alter its specificity for the predetermined (interfering) target immunoglobulin or fragment thereof, which has to be displaced according to the method of the invention.

Basically, the negative charge of the modified antibody shall be increased such that its position relative to its electrophoretic mobility in the gel, specifically the agarose gel, is no longer in the gamma region. The modified antibody should therefore migrate towards the anodic side of the gel, to reach a position that is more anodic with respect to the position that can be attained by the same non-modified antibody of origin.

The quantity of negative electric charges of an antibody or a modified antibody, and especially the increase in the quantity of negative electric charges in the modified antibody, can be estimated through the determination of the electrophoretic mobility of said antibody or modified antibody.

The electrophoretic mobility of a molecule (pep) is directly proportional to the net electric charge of said molecule, according to the Debeye-Huckel-Henry equation $\mu ep=q/6\pi\eta R$, wherein q is the net electric charge of the molecule, $\eta$ is the viscosity of the medium and R is the ionic radius of the molecule.

According to a particular embodiment, the modified antibody has an increased electrophoretic mobility with respect to the electrophoretic mobility of the non-modified antibody of origin, taken in the same conditions. The increase in the electrophoretic mobility is the result of a modification, especially a chemical modification of the antibody as disclosed herein.

Electrophoretic mobility of a modified antibody according to the invention can be evaluated by capillary electrophoresis in free solution, for example on an Agilent CE apparatus equipped with an UV-Vis detector, the electrophoretic mobility being expressed in $cm^2N.S$. An example of conditions suitable for accordingly evaluating electrophoretic mobility of such modified antibody with a CE technique are: Analysis buffer: TrisNeronal 70 mM, pH 9.2, Capillary of 25 μm diameter and 33 cm long, Migration temperature: 22° C. and Voltage: 14 kV.

According to a particular embodiment, by "increased electrophoretic mobility", it is meant that the ratio of the electrophoretic mobility of the modified antibody (pep modified) over the electrophoretic mobility of the native antibody (pep native) is above 1. The electrophoretic mobility pep can be conventionally measured in $cm^2N.S.$, especially with a system as disclosed above, According to a particular embodiment, said ratio is above 1.5 or above 2.

According to a particular embodiment, said ratio is between 1.5 and 6, or between 2 and 6, or between 3 and 6, or between 4 and 6, or between 1.5 and 5, or between 2 and 5, or between 3 and 5, or between 4 and 5.

For example, it has been calculated that for the polyclonal anti-IgG antibody modified with 1,2, 4-benzenetricarboxylic anhydride used in Example 6 herein, for example the ratio is about 4.6, said ratio of about 4.6, meaning that the electrophoretic mobility of the native antibody has been increased by 4.6 and accordingly that the modified antibody bears about 4.6 times more negative charges than the native, non-modified, antibody.

For example, it has been similarly calculated that for the anti-human Trastuzumab modified antibody of Example 2, said ratio is about 2.4, accordingly meaning that the electrophoretic mobility of the native antibody has been increased by 2.4 and that the modified antibody bears about 2.4 times more negative charges than the native, non-modified, antibody.

According to a particular embodiment, the electrophoretic mobility of a modified antibody measured in cm2N.S according to the protocol disclosed herein is at least equal to or more than the electrophoretic mobility measured for a component naturally electrophoresed outside the "zone of interest" as defined herein. For example, said electrophoretic mobility of a modified antibody may be at least equal to or more than the electrophoretic mobility of human albumin, measured according to a conventional protocol, such as the protocol disclosed above.

According to a particular embodiment, the considerations developed above regarding the electrophoretic mobility of a modified antibody used within the present invention similarly apply to the electrophoretic mobility of an immunocomplex formed between a target immunoglobulin or fragment thereof as defined herein and a modified antibody according to the present invention.

According to a particular embodiment however, a modified antibody retains the affinity or the level of affinity of the native antibody for its target immunoglobulin or fragment thereof. Affinity is conventionally measured through a Kd value. Kd values for antibody usually range from low micromolar ($10^{-6}$) to nanomolar ($10^{-7}$ to $10^{-9}$) Kd values and up to the picomolar ($10^{-12}$) Kd values or range for very high affinity antibodies. The fact that the affinity remains sufficient can be appreciated upon the visualization of the results of the method.

It is observed that the affinity of a modified antibody for its immunoglobulin target (also designated displacement efficiency) may be assessed by determining the minimum ratio of the concentration between the modified antibody and the target immunoglobulin that enables full displacement of a determined concentration of the immunoglobulin target to take place. This assessment is obtained experimentally by progressively increasing concentration of the immunoglobulin target while the concentration of the modified antibody remains unchanged, until the displacement of the immunoglobulin target becomes merely partial. This enabled the determination of the ratio values expressed in the following pages, noting such ratio also depends upon the type and titer of the antibody to be modified.

By "having antigenic specificity for a predetermined target immunoglobulin or fragment thereof that may be present in the biological sample" and "having the capacity/capability to form an immunocomplex with said predetermined target immunoglobulin or fragment thereof", it is meant that implementation of the method of the invention requires that the multivalency and/or charge density of the modified antibody enables its displacement outside the region of interest as defined herein, especially outside the gamma region of the gel, without affecting the real capacity of the antibody to bind and shift its antigen, which is the predetermined target immunoglobulin or fragment thereof.

According to a particular embodiment, the modified antibody has lost its capacity to precipitate in the electrophoretic gel used in the method of the invention, as defined herein. The same applies to immunocomplex(es) involving such a modified antibody.

Accordingly, the immunocomplex formed between the modified antibody used in the present invention and the predetermined target immunoglobulin or fragment thereof has an electrophoretic mobility that enables a faster migration in the gel, enabling migration of the immunocomplex to a zone located outside the zone of interest as defined herein, in particular outside the gamma zone of the gel, whereas a target immunoglobulin or fragment thereof that would not be bound to such a modified antibody would stay in said zone of interest, especially gamma zone.

Any method for modifying antibody that allows increasing its negative charge, without altering of its specificity may be employed.

According to a particular embodiment, the increase in negative charge is achieved according to the technical explanations provided herein.

According to a particular embodiment, the modified antibody is a reaction product of an antibody with a carboxylic acid anhydride. The general formula of carboxylic acid anhydrides is $R_1$—CO—O—CO—$R_2$, and $R_2$ being identical or different organic groups and/or hydrogen atom. Carboxylic acid anhydrides as defined herein encompass dianhydrides encompassing two acid anhydride functions, or tricarboxylic anhydrides.

According to a particular embodiment, a modified antibody according to the present disclosure is chemically modified by using an anhydride such as 1,2,4-benzenetricarboxylic anhydride which reacts efficiently with primary amino groups and a hydroxyl functions contained in immunoglobulins and provides to them a certain amount of additional carboxylic acid functions, thus additional negative charges in alkaline pH buffer of the agarose gel matrix.

According to other particular embodiments, the modified antibody is a reaction product of an antibody with an carboxylic acid anhydride, in particular a carboxylic acid anhydride that is 1,2,4-benzenetricarboxylic anhydride or a dianhydride selected amongst: pyromellitic dianhydride (1,2,4,5 benzene tetracarboxylic anhydre), benzophenone-3, 3',4,4'-tetracarboxylic dianhyd ride, diethylenetriaminepentaacetic dianhyd ride.

According to a particular embodiment, the concentration of the carboxylic acid anhydride used for the antibody modification reaction is adapted so as to obtain a suitable electrophoretic mobility of the resulting modified antibody, according to the considerations developed above. In particular, an increase of the concentration of carboxylic acid anhydride used may increase the quantity of negative electrical charges added to the resulting modified antibody, and thereby its electrophoretic mobility.

It has been found that the saturation of all amino and hydroxyl groups contained in an antibody can be reached if an excess of 1,2, 4-benzenetricarboxylic anhydride is used. By "excess", it is meant that the electrophoretic mobility of the resulting modified antibody stops increasing with the concentration of carboxylic acid anhydride used, and/or that the molecular weight of the modified antibody increases with respect to the molecular weight of the native antibody (molecular weight can be conventionally be measured in KDa. An increase in molecular weight can be associated with antibody cross-linking).

According to a particular embodiment, the concentration of carboxylic acid anhydride used for antibody modification is from 10 mM and 200 mM in particular from 50 mM to 160 mM. According to a particular embodiment, the concentration of carboxylic acid anhydride used for polyclonal antibody modification is equal or below 200 mM or equal or below to 150 mM, in particular from 50 mM to 200 mM in particular from 100 to 150 mM.

According to a particular embodiment, the concentration of carboxylic acid anhydride used for monoclonal antibody modification is equal or below 75 mM, in particular from 10 mM to 75 mM. According to a more particular embodiment, the carboxylic acid anhydride used for antibody modification is 1,2,4-benzenetricarboxylic anhydride, used within the ranges disclosed in any of the paragraphs above.

According to a particular embodiment, modification of the antibody is achieved using a concentration of anhydride avoiding a significant loss in the capacity of the antibody to bind to the target immunoglobulin or fragment thereof. By "significant loss" it is meant that the modified antibody is not suitable for appropriately binding the target immunoglobulin or fragment thereof for the purpose of achieving the method described herein. According to a particular embodiment, such concentrations are as disclosed in the paragraphs above.

According to a particular embodiment, the concentration of the antibody to be modified with carboxylic acid anhydride is adapted so as to avoid linkage between modified antibody molecules, which may later impact the specificity of the resulting modified antibody. Linkage between modified antibody molecules can conventionally easily be appreciated by the skilled person when measuring the molecular weight of the resulting antibody. The skilled person will therefore easily determine the appropriate antibody concentration to use.

According to a particular embodiment, the concentration of the antibody to be modified for antibody modification purpose is from 0.1 to 30 g/L.

According to a particular embodiment, the concentration of polyclonal antibody used for polyclonal antibody modification is below 30 g/L, in particular from 3 to 30 g/L.

According to a particular embodiment, the concentration of monoclonal antibody used for monoclonal antibody modification is below 10 g/L, in particular from 0.1 to 10 g/L.

According to a particular embodiment, the modified antibody has the capacity/capability to form an immunocomplex with a predetermined target immunoglobulin or fragment thereof, wherein the immunocomplex is soluble within an electrophoretic gel, in particular the electrophoretic gel used with the method of the invention. By "soluble immunocomplex", it is meant a complex that does not precipitate or is not found in a precipitated form in a medium that is an electrophoretic gel as defined herein, especially an electrophoretic gel used for carrying out the method of the invention.

According to a particular embodiment, a modified antibody according to the present invention has lost its precipitating capacity/capability in a medium that is an electrophoretic gel as defined herein, especially an electrophoretic gel used for carrying out the method of the invention. According to a more particular embodiment, a modified antibody according to the present invention has lost its precipitating capacity/capability as defined above, while keeping its capacity to bind and shift its antigen (i.e., the target immunoglobulin or fragment thereof), according to the present disclosure.

It has also been found that the further use of antisera (capture antibodies) directed against at least one of the components of the formed immunocomplex in step d. above enabled precipitation of an immunocomplex formed between a modified antibody as defined herein and a target immunoglobulin or fragment thereof as defined herein.

The results provided in FIG. 7 illustrate that according to the invention, when an immunocomplex, as found in the gel is not incubated with capture antibodies, then said immunocomplex is eliminated from the gel during washing and pumping steps. Such an immunocomplex is "soluble", i.e., not precipitating. Of note, conventional IFE generally requires precipitating immunocomplexes. Surprisingly, the inventors assessed that applying at least one capture antibody enables obtaining precipitated and/or detectable immunocomplexes.

Step d. described above therefore consists in applying at least one capture antibody (or antiserum) on appropriate zone(s) of the electrophoresed gel plate to permit its reaction with target immunoglobulin(s) or fragment(s) thereof and/or determined antibody isotype(s) in conditions enabling the formation of precipitated and/or detectable immunocomplexes. Accordingly, said application of at least one capture antibody (or antiserum) on appropriate zone(s) of the electrophoresed gel plate permits, because of said "reaction", immunofixation of (all) the target immunoglobulin(s) or fragment(s) thereof and/or determined antibody isotype(s) presented in the track.

According to a particular embodiment, said "conditions enabling the formation of precipitated and/or detectable immunocomplexes" are conventional in the context of IFE. In particular, the conventional conditions detailed in reference (1) may be applied, without change.

Capture antibody(ies) can be either specific for one or the other component(s) of the immunocomplex (either target immunoglobulin or fragment thereof or the determined antibody isotype, including a modified antibody isotype), or specific for the immunocomplex taken as a whole, i.e., an immunocomplex formed between a modified antibody and its target monoclonal component/immunoglobulin or fragment thereof or polyclonal antiserum. According to a particular embodiment, capture antibody(ies) is(are) specific for the target immunoglobulin or fragment thereof, especially an human target immunoglobulin or fragment thereof, especially when found within an immunocomplex (for detection purposes).

According to a particular embodiment, capture antibody(ies) aimed at revealing the modified antibody/target immunocomplex have specificity for the target immunoglobulin or fragment thereof within the immunocomplex.

According to a particular embodiment, the immunofixation procedure following the electrophoresis in presence of a modified antibody uses common anti-human immunoglobulins sera (capture antibody(ies)) for typing purposes.

According to a particular embodiment, each track of the gel is incubated with a specific anti human antiserum (polyclonal antibodies to specific immunoglobulin classes and types (IgG, IgA, IgM, IgK, IgL) as capture antibodies.

The invention also relates to a method for obtaining a modified antibody, especially a modified antibody suitable for use in the IFE methods disclosed herein, involving reaction of an antibody as defined and/or disclosed herein with a carboxylic acid anhydride, as defined and/or disclosed herein.

Suitable antibodies that can be accordingly modified can be monoclonal or polyclonal antibodies, as defined or disclosed in any of the embodiments of the present description.

Suitable carboxylic acid anhydrides are as defined or disclosed in any of the embodiments of the present description.

According to a particular embodiment, the carboxylic acid anhydride is 1,2,4-benzenetricarboxylic anhydride.

According to other embodiments, carboxylic acid anhydrides may be selected from the group of dianhydrides compounds such as pyromellitic dianhydride (1,2,4,5 benzene tetracarboxylic anhydre), benzophenone-3,3',4,4'-tetracarboxylic dianhydride and diethylenetriaminepentaacetic dianhydride. Upon reaction with an antibody, these dianhydrides provide more additional negative charges than that obtained with 1,2,4-benzenetricarboxylic anhydride.

According to a particular embodiment, with these compounds having two carboxylic acid anhydride groups, the antibody solution is diluted during its modification with dianhydride, in order to reduce proteins cross-linking rate that can impair antibody specificity and its capacity to bind and displace target immunoglobulin or fragment thereof. The diluted concentration of antibody can be from 0.1 to 30 g/L.

According to a particular embodiment, the concentration of polyclonal antibody used for polyclonal antibody modification is below 30 g/L, in particular is from 3 to 30 g/L.

According to another particular embodiment, the concentration of monoclonal antibody used for monoclonal antibody modification is below 10 g/L, in particular is from 0.1 to 10 g/L.

According to a particular embodiment, the modified antibody is obtained according to the following steps:
  Providing an antibody solution in a concentration as defined in any one of the embodiments disclosed herein, optionally in an appropriate buffer, optionally after diluting said antibody solution to obtain an antibody solution having a concentration from 0.1 to 30 g/L, and
  Adding to said antibody solution a carboxylic acid anhydride dissolved in a suitable anhydrous solvent, in particular an anhydrous solvent selected amongst: dioxolane, dimethylformamide and dimethylsulfoxide, the carboxylic acid anhydride concentration being in particular in a range of concentration as defined herein, especially from 10 mM and 200 mM, in particular from 50 to 160 mM, the addition being performed at a pH from 7.5 to 9, if necessary by appropriate addition of sodium hydroxide, eventually under controlled stirring, in particular at room temperature (i.e., at a temperature from 20 to 25° C.), and
  Optionally, letting the reaction develop during 10 to 20 minutes, in particular 15 minutes, especially at room temperature as defined herein, and
  Recovering the obtained modified antibody.

According to particular embodiments, the provided antibody solution is in a concentration as defined in any one of the embodiments described herein, including in the Examples section. The quantity of provided antibody solution may range from 100 μL to 15 mL, and can suitably be determined by the skilled person in accordance with common practice.

Addition of sodium hydroxide can be conventionally made according to the common knowledge of the skilled in the art. Examples are provided in the experimental section. The skilled person will readily adapt the procedure according to the pH to be maintained, as disclosed herein.

Recovering the obtained modified antibody can conventionally be performed by dialysis.

According to a particular embodiment, addition of an anhydride solution and sodium hydroxide to the provided antibody solution is performed according to a drop by drop scheme: anhydride solution and sodium hydroxide are alternatively added to the reaction medium containing the antibody to be modified, said reaction medium being maintained under stirring, so as to maintain the pH of the reaction medium in the range of 7.5 to 9. Use of an appropriate device such as a pH-Stat titration instrument can facilitate the procedure. Temperature is as indicated above.

According to a particular embodiment, the drop by drop scheme is used for modifying a polyclonal antibody. I may also be used for modifying a monoclonal antibody when the volume of antibody to be modified is relevant.

According to the above, anhydrides and dianhydrides are dissolved in suitable anhydrous solvent such as dioxolane, dimethylformamide and dimethylsulfoxide in order to avoid their reaction with hydroxyl groups of water.

According to a particular embodiment, a defined quantity of 1,2,4-benzenetricarboxylic anhydride is dissolved with dioxolane, and is added drop by drop using conventional means and practice into a antibody solution having a concentration from 0.1 to 10 g/L if the antibody is a monoclonal antibody or a concentration from 3 to 30 g/L if the antibody is a polyclonal antibody (said antibody solution being alkalised with sodium hydroxide) under controlled stirring and pH from 7.5 to 9 at room temperature as defined herein, by using a pH-Stat titration instrument or other conventional apparatus(es) well known in the art. Recovery of the reaction product can be made according to the following procedure: the reaction product obtained from the step of drop by drop addition may be dialyzed against 100 mM phosphate buffer in order to remove solvent (e.g., dioxolane) and the excess of reagents.

According to the procedures disclosed above and herein, the obtained modified antibody possessing additional negative charges is then ready to use for specific displacement of a target immunoglobulin or fragment thereof according to the present disclosure using the immunofixation electrophoresis process described herein.

According to a particular embodiment, the ratio of the concentration of modified antibody specific for the predetermined target immunoglobulin or fragment thereof and the concentration of the predetermined target immunoglobulin or fragment thereof in the analyzed sample is from 0.1/1 to 20/1, preferably from 1/1 to 5/1.

A ratio of 0.1/1 means that 0.1 g/L of modified antibody is sufficient to displace totally 1 g/L of a target immunoglobulin or fragment thereof. A ratio of 20/1 means that 20 g/L of modified antibody is sufficient to displace totally 1 g/L of a target immunoglobulin or fragment thereof.

Concretely and according to a particular embodiment, several aliquot portions of the biological sample to be analyzed are deposited on parallel tracks of the gel plate in step a. defined above for the method of the invention, with at least one track being loaded with at least one modified antibody according to step b. defined above, optionally several tracks being loaded with a modified antibody according to step b.

According to a particular embodiment, at least one track on the gel plate is a reference track which is not submitted to step d. defined above but is instead contacted with a fixative solution rather than with an antiserum, steps a. to c. and optionally e. remaining the same.

According to a particular embodiment, six aliquot portions of the biological sample are deposited on parallel tracks of the gel plate in step a., including a reference track and five tracks that are respectively contacted in step d. with antisera specific to IgG, IgA, IgM, IgK and IgL, with at least one track being loaded with at least one modified antibody according to step b.

According to a particular embodiment, the said aliquot portions are diluted in an appropriate and conventional diluent, before deposit on their respective tracks of the gel plate, according to the conventional practice in the art. In particular, a 1/6 dilution of the biological sample is usually performed for the aliquot portion used for the G track, and a 1/3 dilution of the biological sample is usually performed for the aliquot portion(s) used for ELP (reference), A, M, K, L tracks. Reference dilution is generally 1/3. These dilutions are indicated for information only and cannot limitatively constrain the method disclosed herein: the skilled person can and knows how to readily adapt these dilutions on purpose, in case it is suspected that a higher dilution of the sample may be beneficial for interpretation of the results, in particular when it is know that a high polyclonal background may be suspected or present.

According to a particular embodiment of the invention the method of preparation of the modified antibodies is performed for the preparation of a modified antibody that recognizes and in particular that binds a therapeutic antibody that may be targeted in the assayed biological sample. According to such a particular embodiment, the method of preparation of the modified antibody enables the recovery of a modified antibody that recognizes therapeutic antibodies used in cancer treatment, in autoimmune disease treatment, in inflammatory disease treatment. By way of illustration the modified antibodies may recognize an antibody selected among Adalimumab, Trastuzumab, Ofatumumab, Siltuximab, Rituximab, Bevacizumab, Infliximab, Cetuximab and Efalizumab, Natalizumab, Panitumumab, Tolicizumab,Clenoliximab, Etaracizumab, Visilizumab, Elotuzumab, Nimotuzumab, Ramicirumab, Elotuzumab, Daratumumab, Mapatumumab, Golimumab, Ustekinumab, Nivolumab, and functionally equivalent antibodies, i.e., antibodies having the same antigenic target than the above listed ones.

According to a particular embodiment, the gel plate is divided in several sections enabling running several immunofixation electrophoresis at the same time.

According to a particular embodiment, the method of the invention further comprises a step of comparing the electrophoretic profile(s) obtained by performing the steps a. to d. and optionally e. with electrophoretic profile(s) obtained in the same conditions and with the same biological sample, but in the absence of any modified antibody as defined in step b.

Accordingly, the method of the invention can be run with an IF system such as the Hydrasys® system manufactured by SEBIA.

In this case, the modified antibody can be applied on the gel using a sample applicator or sample loader. Porous membrane applicator may be used to apply modified antibody on the gel. Other devices such as reusable applicators and plastic thin film with slots usually used for applying samples onto the gel electrophoresis may be employed for application of modified antibody on the gel.

Preferably, when using the Hydrasys® IF system, the sample applicator and modified antibody applicator should have the same configuration and the same dimensions in order to be aligned and match with each electrophoresed area (IFE tracks). The modified antibody solution can be loaded on parallel electrophoresed tracks of the gel. The modified antibody may be applied on all sample tracks of the gel (e.g., ELP, G, A, M, K, L tracks) or on specific tracks depending on the target immunoglobulin or fragment thereof to be displaced (G and K; G and L; A and K; A and L; M and K; M and L).

According to another particular embodiment, the modified antibody is applied on an area of the gel that is separated from the sample deposit area, being on the same track but at a position that is more cathodic with respect to the position of the sample deposit area, in particular between the cathodic extremity of the gel plate and the sample deposit area, for each track that is concerned. According to a more particular embodiment, the distance between the modified antibody application point and that of sample is equal or less than 5 mm.

According to a particular embodiment, especially when the conventional loader used with the Hydrasys® system are used, the distance between the modified antibody application point and that of sample is 5 mm.

According to another particular embodiment however, the deposit area of the at least one modified antibody according to the method described herein is at a distance of sample deposit area that is less than 5 millimeters, in particular from 2 to 3 millimeters, more particularly at a distance of 2 or 3 millimeters.

According to a particular embodiment, the modified antibody is applied on the gel before the sample application. According to another embodiment, the modified antibody is loaded on the gel after the sample application or during the sample application.

According to an advantageous embodiment when using the Hydrasys® system, the modified antibody is applied onto the gel during the sample application, because in this situation there is no change in the immunofixation program already present in said semi automatic instrument.

According to another aspect, it has also been found that a good capacity of the modified antibody to bind and displace a target immunoglobulin or fragment thereof can be reached when sample deposit area and modified antibody application point are very close to one another (sample application point closer to the anodic side of the gel, and modify antibody application point closer to the cathode side of the gel).

Therefore, according to another particular embodiment, the deposit area of the at least one modified antibody according to the method described herein is at a distance of sample deposit area that is less than 3 millimeters, in particular from 0 to 3 millimeters.

In fact, according to a particular embodiment, the modified antibody is applied on an area of the gel that coincides with the sample deposit area, for each track that is concerned. The distance discussed in the above paragraphs is accordingly of 0 millimeters. In this case, it will be understood that according to the invention, the modified antibody and the sample deposit are then deposited on the gel separately, although in any order. According to a particular embodiment, the modified antibody is deposited before the sample deposit at that point. In another embodiment, the modified antibody is deposited after the sample deposit at that point According to a particular embodiment, the immunofixation electrophoresis method described herein is carried out in buffer solution(s) commonly used in the art and for IFE, such as TrisNeronal buffer, at conventional pH(s), for example using a TrisNeronal buffer at pH 9.2, during a conventional time for carrying IFE according to usual protocols, such as 15 minutes or less, and at a conventional temperature, such as 20° C. These parameters can readily be adjusted according to the practice or recommendations of the manufacturer(s) of IFE devices.

According to a particular embodiment, the migration of samples and modified antibody is carried out in 15 minutes or less at 20 Watts.

According to a particular embodiment, the migration of samples and modified antibody is carried out at 20° C.

According to a particular embodiment, the migration of samples and modified antibody is carried out in 15 minutes or less at 20 Watts and at 20° C.

According to a particular aspect, application-time on the gel of modified antibodies according to the present disclosure and sample(s), before beginning of the electrophoresis (migration), may last about 1 minute, in particular is 1 minute.

According to a particular aspect, incubation time on the gel of capture antibody(ies) according to the present disclosure, may last about 5 minutes, in particular is 5 minutes.

Incubation times can be readily adapted by the skilled person seeking a better sensitivity, according to standard practice in the field.

According to a particular embodiment, the method of the invention further comprises a step of staining the gel upon completion of the electrophoresis.

According to a more particular embodiment, staining of the immunocomplexes formed in step c.and optionally step d. described above with respect of the method of the invention can be achieved according to conventional methods, for example with amido black, acid violet, or coomassie red reagent(s). Staining can also be achieved using a marker.

A method as described herein may also further comprises a step of analyzing and/or interpreting the IFE results and/or concluding about the health status of the patient, the biological sample of which has been subjected to a method as described herein.

The invention further relates to a method for detection of interfering immunoglobulin(s) or fragment(s) thereof suspected to be present in the biological sample of a patient, comprising the step of performing at least one immunofixation electrophoresis (IFE) analysis method as described herein on a sample drawn from a patient, wherein the predetermined target immunoglobulin(s) or fragment(s) thereof targeted in said IFE method(s) is(are) said suspected interfering immunoglobulin(s) or fragment(s) thereof.

According to a particular embodiment, by "interfering immunoglobulin(s) or fragment(s) thereof", it is meant monoclonal component(s) or monoclonal therapeutic antibody(ies) as defined herein.

The present invention also discloses a kit that may be used in conjunction with known immunofixation method(s) or kit(s), especially when said method is run on an Hydrasys® instrument, and possibly with the use of existing kit(s) appropriate for IFE, without any change in the conventional immunofixation procedure with respect to the sample preparation and choice of the instrument program.

Are especially required in such a kit, the presence of at least one modified antibody against predetermined target immunoglobulin(s) or fragment(s) thereof, as disclosed herein, and the presence of a further applicator for applying modified antibodies onto the gel before the electrophoresis process, at a deposit point as described herein.

The invention therefore relates to a kit suitable for carrying out a method according to the present disclosure, if appropriate in combination with known kit(s), said kit of the invention comprising or consisting of:

Modified antibody(ies) against target immunoglobulin(s) or fragment thereof as defined and/or disclosed herein, and Applicator(s) for applying said modified antibody(ies) onto the gel, according to the description provided herein for the deposit point(s), and Optionally, mask(s) for applying the modified antibody (ies) on the applicator(s), in order to apply said modified antibody(ies) on appropriate lane(s) of the electrophoretic gel.

The skilled person can appropriately select the lane(s) of the electrophoretic gel on which modified antibody(ies) should be applied, considering the guidance provided herein.

Such a kit may be used in combination with known kit(s), the latter of which may encompass one or several of the following element(s): agarose gel(s), buffer(s), staining reagent(s) and optionally diluent(s) for said staining reagent(s), fixative solution(s), suitable for enabling the formation of precipitated and/or detectable immunocomplexes, as defined herein, filter paper(s) for absorbing moisture and/or excess reagent(s) or solution(s) off the gel surface, and/or absorbing unprecipitated protein(s) off the gel, and optionally antisera reagent(s) as capture antibodies and optionally appropriate diluent(s), comb(s) or any other suitable applicator (s) for sample application or masks(s).

In a particular embodiment, the modified antibody(ies) is(are) a modified antibody that recognizes an antibody selected among Adalimumab, Trastuzumab, Ofatumumab, Siltuximab, Rituximab, Bevacizumab, Infliximab, Cetuximab and Efalizumab, Natalizumab, Panitumumab, Tolicizumab, Cleneliximab, Etaracizumab, Visilizumab, Elotuzumab, Nimotuzumab, Ramicirumab, Elotuzumab, Daratumumab, Mapatumumab, Golimumab, Ustekinumab, Nivolumab, and functionally equivalent antibodies, i.e., antibodies having the same antigenic target than the above listed one. In a particular embodiment, the modified antibody(ies) present in the kit is(are) provided as a ready to use solution such as disclosed herein.

The interpretation of the results of conventional IFE experiments can be straighforward for the skilled in the art, except in certain situations. In fact, current IFE methods do not always avoid the presence of confusing patterns.

A short summary of the conclusions that can be drawn from IFE results, when unambiguous, as well as a summary of the difficulties that can be encountered for results interpretation is provided hereafter.

Absence of Monoclonal Component

A normal serum sample shows a light diffused staining of polyclonal immunoglobulins in all tracks.

A hypergammaglobulinemia is characterized by a heavily stained, diffused gamma zone and absence of any restricted bands. However, this pattern does not exclude the possibility of the presence of discrete monoclonal protein(s). The present invention aims at overcoming the problem related to the presence of these monoclonal protein(s).

Presence of a Monoclonal Component

The presence of a monoclonal protein (gammopathy) is characterized by a monoclonal band detected with one of the anti-heavy chain antisera (gamma, alpha or mu) and either with anti-kappa or anti-lambda light chain antiserum. The detected monoclonal band must be located at the same migration distance as the suspect monoclonal band seen in the reference track (ELP).

Absence of reaction with any of the applied anti-heavy chain antisera and reaction with one of the light chain antisera might indicate a very rare Ig D or Ig E gammopathy. A next step would be to confirm this hypothesis by performing an IFE with anti-delta or anti-epsilon heavy chain antisera. This result may also indicate a light chain gammopathy. A next step would be to confirm this hypothesis by performing an IFE with antisera anti-kappa or anti-lambda free light chains.

Failure to observe a positive reaction with any of the applied anti-light chain antisera, while an anti-heavy chain antiserum reacts, might indicate a very rare heavy chain gammopathy (gamma, alpha, delta or mu). In these cases it would be recommended to use another method to confirm the result (e.g., immunosubstraction by capillary electrophoresis or immunoprecipitation in tube by increasing incubation time of sample with anti-light chain antisera). The present invention overcomes this problem of having recourse to another method.

Presence of Two or More Monoclonal Components

In some cases, several clones of B-cells proliferate as indicated by several monoclonal bands can be revealed by immunofixation:

A biclonal gammopathy is characterized by the presence of two bands of heavy chain (identical or different) and two bands of light chains (identical or different). Occasionally, these biclonal bands could co-migrate and thus render the interpretation difficult. The present invention defines means that aim at overcoming this problem.

An oligoclonal gammopathy is characterized by the presence of multiple, usually weak bands of one or more types of heavy chains and by one or two types of light chains. Occasionally, one of these bands may be relatively prominent. However, detection of an oligoclonal gammopathy in the presence of a significant polyclonal background may be dubious. Owing to the difficulty to interpret this type of IFE patterns, it is generally be recommended to repeat the IFE in 3 to 6 months. The present invention aims at overcoming this problem.

It is also recommended to use high resolution gel(s) for immunofixation procedures to obtain a better resolution in gamma zone where elongated gammaglobulin zone allows multiple bands visualization, which is time consuming.

Special Cases

For some Ig A gammopathies, the anti-light chain antiserum may present a faint affinity with the corresponding monoclonal immunoglobulin, and its detection is more difficult. In that case, it is recommended to test the sample with a Bence Jones immunofixation procedure where the antiserum reaction is amplified due to a longer incubation time. the present invention aims at overcoming this problem.

For some Ig D gammopathies, the anti-light chain antiserum may present a faint affinity with the corresponding monoclonal immunoglobulin, and its detection is more difficult. The present invention aims at overcoming this problem by applying modified anti kappa or modified anti lambda on the track where anti IgD for immunofixation will be loaded.

For some Ig E gammopathies, the anti-light chain antiserum may present a faint affinity with the corresponding monoclonal immunoglobulin, and its detection is more difficult. The present invention aims at overcoming this problem by applying modified anti kappa or modified anti lambda on the track where capture anti IgE will be loaded.

With polyclonal background, it can be recommended to use higher dilution of the sample for antisera tracks, and especially for IgG track. But some time the process of dilution is not successful as the monoclonal protein might be also diluted. Then possible loss of very thin bands presents in the polyclonal background as polyclonal does not exclude the possibility of the presence of monoclonal protein. In fact, adaptation of the dilution factor applied to the assayed sample is a common practice, performed by the skilled user of IFE, on the basis of guess work. However, even a skilled user may choose a non-successful dilution factor, as explained above. The present invention aims at overcoming this problem.

From the above, it can be seen that in several cases interpretation of the results of the IFE performed using current conventional methods can be difficult. Generally, the presence of so-called interfering component(s) that can co-migrate on an IFE gel renders the interpretation more difficult. As illustrated in the Examples below, the disclosed invention successfully enables to overcome these limitations.

In addition, other features of the invention will be apparent when reading the examples and the figures, which illustrate the experiments conducted by the inventors, in complement to the features and definitions given in the present description. The examples are however not limitative with respect to the described invention.

LEGEND OF THE FIGURES

FIG. 1. (1A) Applicator carrier adapted to Hydrasys® device loaded with combs at position 3, 8 and 9. (1) shows the samples applicators (combs) located at positions 3 and 9, (2) shows the modified antibody's applicator (comb) located at position 8 (1B) Applicator carrier adapted to Hydrasys® device with combs well aligned with IF agarose gel tracks. (3) shows the agarose gel, (4) shows the cathodic side of the gel, (5) shows the anodic side of the gel.

FIG. 2. Improved IFE method based on on-gel immunodisplacement of adalimumab for analysis of serum sample spiked with Adalimumab, using modified monoclonal antibody anti Adalimumab (with 1,2,4-benzenetricarboxylic anhydride). IF result 1: normal serum sample; applied on the gel at comb position 3 of applicator carrier adapted to Hydrasys® device. IF result 2: normal serum sample spiked with Adalimumab 1 g/L applied on the gel at comb position 3 of the applicator carrier. IF result 3=IF result 4: normal serum sample spiked with Adalimumab 1 g/L (applied on the gel at comb position 9 of the applicator carrier) that is immunodisplaced in tracks G and K, using modified monoclonal antibody anti-Adalimumab, loaded in wells 3, 6, 10 and 13 of an additional applicator adapted to Hydrasys® device located in position 8 of the applicator carrier. (6) shows the track G with Adalimumab displaced (G-Adalimumab), (7) shows the track K with Adalimumab displaced (K-Adalimumab), (8) shows the Adalimumab in tracks G and K, (9) shows the complexes between the Adalimumab and modified anti-Adalimumab.

FIG. 3. (3A) Improved IFE method based on on-gel immunodisplacement of Trastuzumab in order to mitigate Trastuzumab contained in serum sample, using modified monoclonal antibody anti-Trastuzumab (with 1,2, 4-benzenetricarboxylic anhydride). IF result 1: normal serum sample; applied on the gel using position 3 of the applicator carrier adapted to Hydrasys® device. IF result 2: normal serum sample spiked with Trastuzumab 0.25 g/L; applied on the gel with comb position 3. IF result 3=IF result 4: normal serum sample spiked with Trastuzumab 0.25 g/L (applied on the gel with comb position 9) that is immunodisplaced in tracks G and K, using modified monoclonal antibody anti-Trastuzumab, loaded in wells 3, 6, 10 and 13 of the additional applicator located in position 8 of applicator carrier. (10) shows the track G with Trastuzumab displaced (G-Trastuzumab), (11) shows the track K with Trastuzumab displaced (K-Trastuzumab), (12) shows the Trastuzumab in tracks G and K, (13) shows the complexes between the Trastuzumab and modified anti-Trastuzumab.

(3B) Improved IFE used to mitigate Nivolumab contained in serum sample using modified monoclonal antibody anti-Nivolumab (with 1,2, 4-benzenetricarboxylic anhydride). IF result 1: normal serum sample spiked with Nivolumab 1 g/l, where Nivolumab appears as GK band (Legend: Arrows (1)). IF result 2: is Improved IFE result of the same serum sample where one can observe displacement of GK band out of the gamma zone. IF result 3 and IF result 4: are repeated improved IFE of the same sample spiked with Nivolumab. IF results 2, 3 and 4 shows the position of Nivolumab and anti Nivolumab complex in tracks G and K. Legend: Arrows (2): Nivolumab/anti nivolumab complex.

(3C) Improved IFE used to mitigate daratumumab contained in serum sample using modified monoclonal antibody anti-daratumumab (with 1,2,4-benzenetricarboxylic anhydride). IF result 1: normal serum sample spiked with daratumumab 1 g/l, where daratumumab appears as GK band (Legend: Arrows (1)). IF result 2: is Improved IFE result of the same serum sample where one can observe displacement of GK band out of the gamma zone. Improved IFE IF results 2 also shows the position of daratumumab and anti anti-daratumumab complex in tracks G and K. Legend: Arrows (2): daratumumab/anti daratumumab complex.

(3D) Improved IFE used to mitigate together daratumumab and Nivolumab contained in serum sample using a mixture of modified monoclonal antibody anti-daratumumab and modified monoclonal anti-Nivilumab IF result 1: normal serum sample spiked with daratumumab 0.5 g/l and Nivolumab 0.5 g/l, where daratumumab and Nivolumab appear as 2 GK bands. IF result 2; result 3 and result 4 are repeated results of Improved IFE of the same serum sample where one can observe displacement of the 2 GK bands out of the gamma zone. Legend Arrow (1) Nivolumab, Arrow (2) daratumumab.

(3E) Improved IFE used to mitigate only Nivolumab contained in serum sample already containing Elotuzumab (another therapeutic monoclonal antibody) using modified monoclonal anti-Nivilumab IF result 1: normal serum sample spiked with Elotuzumab 0.5 g/l and Nivolumab 0.5 g/l, where Elotuzumab and Nivolumab appear as 2 GK bands. IF result 2; result 3 and result 4 are repeated results of Improved IFE of the same serum sample where one can observe the displacement of only the GK band corresponding to Nivolumab out of the gamma zone, demonstating the specificity of the method. Legend Arrows (1) and (3): Elotuzumab, Arrow (2) Nivolumab FIG. 4. (4A) Improved IFE used in case of oligoclonal gammopathy (sample C) having significant polyclonal background in G track of a "classical" IF, using modified anti IgK and anti IgL (with 1,2,4-benzenetricarboxylic anhydride). IF result 1=IF result 2 are repeated results of sample C with classical IF method (applied twice on the gel using applicator position 3 of applicator carrier). IF result 3 is improved IFE result of Sample C (applied on the gel using comb position 9) where IgK component is immunodisplaced in track G (G-IgK), using modified anti IgL loaded in well 3 of the additional applicator located in position 8 of applicator carrier. IF result 4 is improved IFE result of Sample C (applied on the gel with comb position 9) where IgL component is immunodisplaced in track G (G-IgL), using modified anti IgL loaded in well 10 of the additional applicator located in position 8 of applicator carrier. (14) shows the track G with IgK component displaced (G-IgK), (15) shows the track G with IgL component displaced (G-IgL), (16) shows Band C1 (not visible in track G of IF result 1), (17) shows the IgK/modified anti IgK complex, (18) shows the IgL/modified anti IgL complex.

(4B) On-gel immunodisplacement of IgK and IgL components from G track of sample D using of modified anti IgK and anti IgL (with 1,2,4,5 benzene tetracarboxylic anhydre or pyromellitic dianhydride), in case of oligoclonal gammopathy having significant polyclonal background, followed by Immunofixation. IF result 1=IF result 2 are repeated results of sample D with classical IF method (applied twice on the gel using applicator position 3 of applicator carrier). IF result 3 is improved IFE result of Sample D (applied on the gel using comb position 9) where IgK component is immunodisplaced in track G (G-IgK), using modified anti IgK loaded in well 3 of the additional applicator located in position 8 of applicator carrier. IF result 4 is improved IFE result of Sample D (applied on the gel with comb position 9) where IgL component is immunodisplaced in track G (G-IgL), using modified anti IgL loaded in well 10 of the additional applicator located in position 8 of applicator carrier. (19) shows the track G with IgK component displaced (G-IgK), (20) shows the track G with IgL component displaced (G-IgL), (21) shows Band D1(not visible in track G of IF result 1), (22) shows the IgK/modified anti IgK complex, (23) shows the IgL/modified anti IgL complex.

FIG. 5. (5A) Improved IFE method for resolving cases of IgA gammopathies without any corresponding light chain by using modified anti IgK and anti IgL (with 1,2,4-benzenetricarboxylic anhydride). IF result 1 is classical IFE result of sample E; applied on the left side the gel (bottom row) using applicator position 3 of applicator carrier. IF result 2 is improved IFE result of Sample E; applied on the right side of the gel (bottom row) using applicator position 3 of applicator carrier, where IgK component is immunodisplaced in track A (A-IgK), using modified anti IgL loaded in well 11 (to be aligned with track A) of the additional applicator located in position 2 of applicator carrier. IF result 4 is improved IF result of Sample E (applied on the gel with applied on the gel with applicator position 9) where IgL component is immunodisplaced in track A (A-IgL), using modified anti IgL loaded in well 11 of the additional applicator located in position 8 of applicator carrier. (24) shows the track A with IgK component displaced (A-IgK), (25) shows the track A with IgL component displaced (A-IgL), (26) shows the IgA/modified anti IgL complex. (5B) Improved IFE method applied in case of IgD gammopathy without any visible corresponding light chain on classical immunofixation in serum sample, by using modified anti IgK and anti IgL (with 1,2,4-benzenetricarboxylic anhydride).

FIG. 5 B shows IFE results of sample E' where IgD band does not react (or cannot be visualized in tracks K and L because of their high polyclonal background) with capture anti IgK and anti IgL, but is displaced by modified anti IgK. The reaction of modified anti IgK with IgD band means that the corresponding light chain is IgK, then sample E' is characterized as DK.

Legend Arrow (1): IgD/anti IgK complex, Arrow (2): IgD band not displaced with modified anti IgL.

FIG. 6. (6A) Improved IFE method applied in case of biclonal gammopathy with co-migration of bands (GK+GL): On-gel immunodisplacement of IgG and IgL respectively in tracks L and G, using modified anti IgG and modified anti IgL (with 1,2,4-benzenetricarboxylic anhydride), followed by immunofixation in case of sample F. IF result 1=IF result 2 are repeated classical IFE results of sample F (applied twice on the gel using applicator position 3 of applicator carrier). IF result 3 is improved IFE result of Sample F (applied on the gel using comb position 9) where band F1 is immunodisplaced in track L using modified anti IgG (L-IgG) loaded in well 7 of the additional applicator located in position 8 of applicator carrier. IF result 4 is improved IFE result of Sample F (applied on the gel with comb position 9) where IgL component is immunodisplaced in track G (G-IgL), using modified anti IgL loaded in well 10 of the additional applicator located in position 8 of applicator carrier. (27) shows the track L with IgG component displaced (L-IgG), (28) shows the track G with IgL component displaced (G-IgL), (29) shows Band F1, (30) shows the IgL/modified anti IgG complex, (31) shows the IgG/modified anti IgL complex.

(6B) Shows Improved IFE method for resolving cases of biclonal gammopathy GK+MK where the two different bands of heavy chain and the identical band of light chains are located at the same position on the electrophoresis pattern, and where the M band is suspected to not have a corresponding light chain. (Sample G)

FIG. 6-B, IF result 1 is the IFE result of sample G showing the co-migrating bands on tracks G, M and K. In this case, the interpreter will wonder if this IgM possess a corresponding light chain or not.

FIG. 6-B, IF result 2 shows improved IFE result of sample G, after on-gel immunodisplacement of IgK molecule on track M using modified anti IgK polyclonal. The displacement of M band with modified anti IgK polyclonal is indicative of the presence of MK in this sample. Then sample G is characterized as GK and MK.

Legend Arrow (1): IgM/anti IgK complex

FIG. 6-B, IF result 3 shows another improved IFE result with sample G, after on-gel immunodisplacement of IgL molecule on track M using modified anti IgL polyclonal, where there is no displacement of M band with modified anti IgL.

FIG. 7. Results demonstrating that when the complex on the gel is not incubated with capture antibodies (results on the right side of the gel), then a daratumumab/modified anti-daratumumab complex (which is not precipitating) is eliminated from the gel during washing and pumping steps. IF Result 1=Improved IFE result of Normal serum sample spiked with daratumumab. IF Result 2=Improved IFE result of Normal serum sample spiked with daratumumab, but without immunofixation of daratumumab/modified antidaratumumab complex position on the gel. Legend (1): Incubation zone of capture antibodies (G, A, M, K, L)

MATERIALS AND METHODS—GENERALITIES

The principle of the "On-gel Immunodisplacement" technique followed by immunofixation according to the present invention has been implemented on the state of the art Hydrasys® electrophoresis system (SEBIA), a semi-automated multi-parameter instrument, according to the recommendations of the manufacturer. Reference is made regarding the features of this device to the available Instruction Manual Ref 1201-release 2.2x 2015/03 readily available upon request or provided with commercialized apparatuses so far.

The On-gel immunodisplacement and immunofixation technique of the present invention was carried out on Hydrasys®, with the Immunofixation program being performed with the Hydragel IF kit from start to finish. Hydragel IF kit is a commercialized kit comprising agarose gels, buffered strips, acid violet or amidoblack stains, sample diluent, applicators for samples application, filter papers, filter paper combs (standard mask reference PN 1255), antisera segments (dynamic mask reference PN 1260). Antiserums anti-G, A, M, K, L, Kfree, Lfree are provided separately but conventional in the field.

The loading of samples on the agarose immunofixation gel simultaneously with modified antibody against the target immunoglobulin(s) or fragment thereof was achieved by using one porous membrane comb for diluted samples and an additional comb for the modified antibody.

Samples comb was hang on at a position different to that of the modified antibody. In FIG. 1A and FIG. 1B, the sample's applicators are located at position 3 and 9 and modified antibody's applicator is placed at position 8 of sample applicator carrier, in order to displace target immunoglobulin or fragment thereof contained in the samples applied on the gel with position 9 comb.

The distance between position 8 and 9 was 5 mm and position 8 was near the cathodic side and position 9 was near the anodic side of the gel.

Migration of samples and modified antibody was carried out in less than 15 min at 20 W at 20° C.

Each track of the gel was then incubated with specific anti human (polyclonal antibodies to specific immunoglobulin classes and types (IgG, IgA, IgM, IgK, IgL) by using specific Dynamic Mask or Standard Mask commercialized by Sebia and known in the art (references above).

The gel was automatically washed, stained with Acid Violet, distained and dried.

Principle of the Designed Method Carried out on Hydrasys® Device

FIG. 1 (1A and 1B) shows the applicator carrier adapted to Hydrasys® device with a possibility to hang on and apply simultaneously 13 (1, 2, 3 . . . 13) different sample applicators onto the gel. The gap between each applicator arranged on the device is 5 mm.

This device can then allow simultaneous application of the modified antibody and samples onto the gel. This piece of equipment also allows sample application area and application point of modified antibody to be well aligned on the gel during the electrophoresis process.

Depending on the gel format, the user may choose to perform immunodisplacement of target immunoglobulin or fragment thereof on a single row samples or on all rows samples of the gel. The user can also choose to perform immunodisplacement in specific IF track G, A, M, K or L.

In FIG. 1, the arrangement of applicators on the applicator carrier is illustrated: this arrangement is such that immunodisplacement is performed only with samples applied on the gel with the applicator position 9 using a modified antibody loaded on the gel with applicator at position 8. Samples deposited with applicator position 3 (bottom row) were not immunodisplaced with modified antibody and were used as reference.

The concentration of modified antibody applied on the gel may be higher or less than that of the target immunoglobulin or fragment thereof contained in the sample. According to a particular embodiment, the ratio of modified antibody and the target immunoglobulin or fragment thereof in terms of concentration may be from 0.1/1 to 20/1. According to more particular, especially preferred, embodiment, the ratio of modified antibody and the target immunoglobulin or fragment thereof in terms of concentration is from 1/1 to 5/1.

When applying an electric field in the gel for electrophoresis process, the modified antibody applied onto the gel in a point that is more cathodic with respect to the sample deposit point, migrates faster owing to its additional negative charges, then, crosses the components present in the deposited sample(s), and binds and shifts specifically the targeted immunoglobulin(s) or fragment thereof outside the zone of interest, especially outside the gamma zone.

Depending on the charge density (and electrophoretic mobility) of the modified antibody and that of the target immunoglobulin(s) or fragment thereof, the position of the resulting immunocomplex (target immunoglobulin(s) or fragment thereof/modified antibody) is located outside the zone of interest as defined herein, in particular can be located from the beta zone to the albumin zone, or from the alpha zone, including alpha1 or alpha2 zone, to the albumin zone.

Since the modified antibody grafted with additional negative charges by reaction with carboxylic acid anhydride as disclosed herein has lost its precipitation capacity, the resulting immunocomplex(es) will no longer precipitate in the gel and will not stay in the gel without its (their) precipitation by using unmodified antisera directed against at least one of the components of said immune complex(es).

Then after proteins separation and immunodisplacement of the targeted immunoglobulin(s) or fragment thereof with the modified antibody, anti-human antisera (unmodified) usually used for IFE (characterized by their precipitation capacity), comprising polyclonal antibodies to specific immunoglobulin classes and types (IgG, IgA, IgM, IgK, IgL, IgKfree, IgLfree) are applied on parallels tracks (G, A, M, K, L) on the gel. The gel and these different antisera are then incubated during a time enabling the formation of another immune complex between the sample proteins and the capture antibodies.

The immunocomplex formed between target immunoglobulin(s) or fragment thereof and modified antibody can generally be recognized and precipitated by antisera conventionally used in IFE. The target immunoglobulin or fragment thereof is generally a human or humanised protein. The antisera can be of animal origin.

All immune complexes are then visualized after staining the gel.

Any conventional reagent allowing staining of the gel may be used (amido black, acid violet, coomassie red).

The appearance of a specific band in gamma region is thus indicative of the presence of a monoclonal protein or component corresponding to a particular immunoglobulin type (IgG, IgA, IgM, IgK,IgL, IgKfree, IgLfree) and the presence of an additional band out of gamma zone, preferably between alpha-1 zone and albumin, is indicative of the complex formed between the targeted immunoglobulin(s) or fragment thereof and the modified antibody.

For a given immune complex, it has been found that the band signal is proportional to the concentration of the target immunoglobulin(s) or fragment thereof present in the sample and is visualized if the target immunoglobulin(s) or fragment thereof concentration is higher than 0.1 g/L, which is the detection limit of Hydragel IF method.

EXAMPLES

Example 1

Improved IFE for Analysis of a Normal Serum Spiked with Adalimumab (Interfering or Target Immunoglobulin)

Adalimumab (Creative Biolabs) is a human monoclonal antibody (IgGK) involved in autoimmune disorders like arthritis, rheumatoid, psoriasis, Crohn's disease. The classical IFE of samples from patients treated with Adalimumab monoclonal antibody show interfering band in ELP, G and K tracks. Improved IFE described in the present invention mitigates this interference as follow:

Preparation of a Modified Monoclonal Antibody (Anti-Adalimumab from Abd Serotec) Having Antigenic Specificity for Adalimumab (Target Immunoglobulin)

Provision of 200 µl of human anti-Adalimumab monoclonal antibody from AbD Serotec (0.5 g/l in PBS solution)

A solution of 0.05 M of 1,2,4-benzenetricarboxylic anhydride was prepared in Dioxolane.

The 200 µl of anti-Adalimumab monoclonal antibody solution was mixed with 4.5 µl of 1 N sodium hydroxide and 24 µl of anhydride solution for 15 min at room temperature.

The reaction product was then dialyzed against phosphate buffer, 100 mM pH 7.4 for a night.

The dialyzed solution of modified anti-Adalimumab was then ready to use for on-gel immunodisplacement of Adalimumab containing in a serum sample.

Improved IFE Method for Mitigating Adalimumab Interference: Specific On-Gel Immunodisplacement of Adalimumab in the Sample Spiked with Adalimumab Followed by Immunofixation Improved IFE method was carried out on Hydrasys® electrophoresis system using Immunofixation program and Hydragel 4 IF kit (possibility of 4 samples per gel).

A membrane porous applicator loaded with 2 samples (FIG. 2, IF result 1: normal serum sample; and FIG. 2, IF result 2: normal serum spiked with Adalimumab 0, 25 g/l), was placed at position 3 of the applicator carrier adapted to Hydrasys® device.

Another comb with porous membrane loaded in all wells with the same sample serum spiked with Adalimumab 0.25 g/L was placed at position 9 of the applicator carrier.

A third comb loaded with modified human anti Adalimumab in wells number 3 (aligned with track G of upper row of the gel IF result 3, FIG. 2), number 6 (aligned with track K of upper row of the gel IF result 3, FIG. 2), number 10 (aligned with track G of upper row of the gel IF result 4, FIG. 2), number 13 (aligned with track K of upper row of the gel IF result 4, FIG. 2) was placed at position 8 of the applicator carrier, in order to displace specifically Adalimumab in the sample on tracks G and Kappa in upper row (FIG. 2 result 3 and 4)

The Hydrasys® immunofixation program was then started to allow all these combs to be simultaneously in contact with agarose immunofixation gel dedicated for 4 samples (4 IF) during 1 minute.

After application of samples and modified anti Adalimumab on the gel, the migration started automatically and was carried out in less than 15 minutes at 20 W at 20° C.

During the migration, the modified anti Adalimumab bounds and shifts specifically Adalimumab molecules containing in tracks G and Kappa of samples deposited at position 9 of the applicator carrier. Each track of the gel was then incubated with a specific anti human (polyclonal antibodies to specific immunoglobulin classes and types (IgG, IgA, IgM, IgK, IgL) (capture antibodies) following Hydragel Immunofixation process, by using specific Sebia Dynamic Mask or Standard Mask.

The gel was automatically stained with Acid Violet and distained before the final-stage drying.

FIG. 2, IF result 1 is the result of normal serum sample.

FIG. 2, IF result 2 is IFE result of normal sample spiked with adalimumab, where the corresponding band is noticeable in tracks ELP, G and Kappa.

FIG. 2, IF results 3 and 4 are IFE results obtained with the spiked normal serum sample, after specific on-gel immunodisplacement of adalimumab in tracks G and kappa using modified ant adalimumab; while bands appearing between alpha 1 and alpha 2 zones on tracks G and Kappa (IF results 3 and 4), are indicative of the position of immune complex formed between Adalimumab and modified anti Adalimumab during migration step.

Example 2A

Improved IFE for analysis of a normal serum spiked with Trastuzumab (interfering or target immunoglobulin). Trastuzumab is a humanized monoclonal antibody used in breast cancer treatment.

The classical IFE of samples from patients treated with Trastuzumab monoclonal antibody show interfering band in ELP, G and K tracks. Improved IFE described in the present invention mitigates this interference as follow:

Preparation of a Modified Monoclonal Antibody (Anti-Trastuzumab from Abd Serotec) Having Antigenic Specificity for Trastuzumab (Target Immunoglobulin)

Provision of 200 µl of human anti Trastuzumab monoclonal antibody from AbD Serotec (0.5 g/l in PBS solution)

A solution of 0.05 M of 1,2,4-benzenetricarboxylic anhydride was prepared in Dioxolane The 200 µl of anti Trastuzumab monoclonal antibody solution was mixed with 4.5 µl of 1N sodium hydroxide and 24 µl of anhydride solution for 15 min at room temperature.

The reaction product was then dialyzed against phosphate buffer, 100 mM pH 7.4 for a night.

The dialyzed solution of modified anti Trastuzumab was then ready to use for on-gel immunodisplacement of Trastuzumab containing in a serum sample.

Improved IFE Method for mMitigating Trastuzumab interference: Specific On-Gel Immunodisplacement of Trastuzumab with the Sample Spiked with Trastuzumab Improved IFE method was carried out on Hydrasys® electrophoresis system using Immunofixation program and Hydragel 4 IF kit (Possibility of 4 samples per gel).

A membrane porous applicator loaded with 2 samples (FIG. 3A, IF result 1: normal serum sample; and FIG. 3A, IF result 2: normal serum spiked with Trastuzumab 1 g/l), was placed at position 3 of the applicator carrier adapted to Hydrasys® device.

Another comb with porous membrane loaded in all wells with the same sample serum spiked with Trastuzumab 1 g/L was placed at position 9 of the applicator carrier.

A third comb loaded with modified human anti Trastuzumab in wells

Number 3 (aligned with track G of upper row of the gel IF result 3, FIG. 3A), Number 6 (aligned with track K of upper row of the gel IF result 3, FIG. 3A), Number 10 (aligned with track G of upper row of the gel IF result 4, FIG. 3A), Number 13 (aligned with track K of upper row of the gel IF result 4, FIG. 3A), was placed at position 8 of the applicator carrier, in order to displace specifically Trastuzumab contained in tracks G and Kappa in upper row (FIG. 3A result 3 and 4).

The Hydrasys® immunofixation program was then started to allow all these combs to be simultaneously in contact with agarose immunofixation gel dedicated for 4 samples (4IF) during 1 minute.

After application of samples and modified anti Trastuzumab on the gel, the migration started automatically and was carried out in less than 15 minutes at 20 W at 20° C.

During the migration, the modified anti Trastuzumab bounds and shifts out of gamma zone specifically Trastuzumab molecules containing in tracks G and Kappa of samples deposited at position 9 of the applicator carrier.

Each track of the gel was then incubated with a specific anti human antiserum (polyclonal antibodies to specific immunoglobulin classes and types (IgG, IgA, IgM, IgK, IgL) following Hydragel Immunofixation process, by using specific Sebia Dynamic Mask or Standard Mask. Any type of applicator may be however used.

The gel was automatically stained with Acid Violet and distained before the final-stage drying.

FIG. 3A, IF result 1 is the result of normal serum sample.

FIG. 3A, IF result 2 is IFE result of normal sample spiked with Trastuzumab, where the corresponding band is noticeable in tracks ELP, G and Kappa.

FIG. 3A, IF results 3 and 4 are IFE results obtained with the spiked normal serum sample, after specific on-gel immunodisplacement of Trastuzumab in tracks G and kappa using modified anti Trastuzumab; while bands appearing between alpha 1 and alpha 2 zones on tracks G and Kappa (IF results 3 and 4), are indicative of immune complex formed between Trastuzumab and modified anti Trastuzumab during migration step.

FIG. 3A shows the results of on-gel immunodisplacement of Trastuzumab using modified anti human Trastuzumab (with 1,2,4-benzenetricarboxylic anhydride) followed by immunofixation.

Trastuzumab (Creative Biolabs) is a humanized monoclonal antibody used in breast cancer treatment.

Since Trastuzumab is a humanized monoclonal antibody, its appear on IFE as a monoclonal band on G and K tracks and could wrongly be marked as endogenous monoclonal protein:

FIG. 3A, IF result 1 [normal sample] and FIG. 3A, IF result 2 [normal sample spiked with Trastuzumab 0.25 g/L, where one can observe a band in tracks G and K.

FIG. 3A, IF result 3 and FIG. 3A, IF result 4 illustrate on-gel immunodisplacement of Trastuzumab in tracks G and K, using modified monoclonal anti trastuzumab antibody, where the sample is a normal sample previously spiked with Trastuzumab 0.25 g/l. The disappearance of band in gamma zone of G and K tracks is well noticeable and one can clearly distinguish the complex Trastuzumab/modified anti trastuzumab appearing on the same tracks (G and K) between alpha1 and alpha 2 zones.

In the same way, Bevacizumab a humanized monoclonal antibody (IgGK) involved in cancer, age related macular degeneration were also immunodisplaced using a modified monoclonal anti Bevacizumab (with 1,2,4-benzenetricarboxylic anhydride) and the gamma zone was totally free of this interference.

The present invention could then be used in conjunction with the immunofixation in order to solve all interferences related therapeutic monoclonal antibodies provided one has the monoclonal antibody against the said drug.

Example 2B

Improved IFE for analysis of a normal serum spiked with Nivolumab (interfering or target immunoglobulin)

Nivolumab is a human monoclonal antibody used in lung cancer, renal cancer, melanoma treatment. The classical IFE of samples from patients treated with Nivolumab monoclonal antibody shows interfering band in ELP, G and K tracks. Improved IFE described in the present invention mitigates this interference as follow:

Preparation of a Modified Monoclonal Antibody (Anti-Nivolumab) Having Antigenic Specificity for Nivolumab (Target Immunoglobulin)

Provision of 500 µl of human anti Nivolumab monoclonal antibody from the supplier (5 g/l in PBS solution)

A solution of 0.05 M of 1,2,4-benzenetricarboxylic anhydride was prepared in DMSO The 500 µl of anti Nivolumab monoclonal antibody solution was mixed with 10 µl of 1 N sodium hydroxide and 50 µl of anhydride solution for 15 min at room temperature.

The reaction product was then dialyzed against phosphate buffer, 100 mM pH 7.4 for a night.

The dialyzed solution of modified anti Nivolumab was then ready to use for on-gel immunodisplacement of Nivolumab contained in a serum sample.

Improved IFE Method for Mitigating Nivolumab Interference: Specific On-Gel Immunodisplacement of Nivolumab with the Sample Spiked with Nivolumab Improved IFE method was carried out on Hydrasys® electrophoresis system using current Immunofixation program and Hydragel 4 IF kit (Possibility of 4 samples per gel). Two membrane porous applicators where loaded with normal serum sample spiked with Nivolumab 1 g/l was placed at position 3 and 9 of the applicator carrier adapted to Hydrasys® device.

Another comb where loaded with modified human anti Nivolumab in wells number 10 and 13 aligned with tracks G and K of bottom row of the gel, and placed at position 2 of applicator carrier.

An additional comb placed at position 8 of applicator carrier where loaded with modified human anti Nivolumab in wells number 3, 6, 10 and 13.

The Hydrasys® immunofixation program was then started to allow all these combs to be simultaneously in contact with agarose immunofixation gel dedicated for 4 samples (41F) during 1 minute.

After application of samples and modified anti Nivolumab on the gel, the migration started automatically and was carried out in less than 15 minutes at 20 W at 20° C.

During the migration, the modified anti Nivolumab bounds and shifts out of gamma zone specifically Nivolumab immunoglobulin in all tracks G and Kappa below which modified anti Nivolumab where applied.

Each track of the gel was then incubated with a specific anti human antiserum (polyclonal antibodies to specific immunoglobulin classes and types (IgG, IgA, IgM, IgK, IgL) following Hydragel Immunofixation process, by using specific Sebia Dynamic Mask or Standard Mask. Any type of applicator may be however used.

The gel was automatically stained with Acid Violet and distained before the final-stage drying.

FIG. 3B, IF result 1 is the classical IFE result of normal serum sample spiked with Nivolumab where a monoclonal band is noticeable in tracks ELP, G and K.

FIG. 3B, IF result 2 is improved IFE result of normal sample spiked with Nivolumab, where the monoclonal band was shifted with modified anti Nivolumab out of gamma zone in tracks G and K, using the additional comd applied on the gel at position 2 of the carrier applicator; while signals appearing at alpha 1 position on tracks G and K are indicative of immune complex formed between Nivolumab and modified anti Nivolumab during migration step FIG. 3B, IF result 3 and result 4 are improved IFE result of normal sample spiked with Nivolumab, where the monoclonal band was shifted with modified anti Nivolumab out of gamma zone in tracks G and K, using the additional comb applied on the gel at position 8 of the carrier applicator; while signals appearing at alpha 1 position on tracks G and K are indicative of immune complex formed between Nivolumab and modified anti Nivolumab during migration step Example 2C Improved IFE Method for Analysis of a Normal Serum Spiked with Daratumumab (Interfering or Target Immunoglobulin)

Daratumumab is a human monoclonal antibody used in multiple myeloma treatment. The classical IFE of samples from patients treated with daratumumab monoclonal antibody shows interfering band in ELP, G and K tracks. Improved IFE described in the present invention mitigates this interference as follow:

Preparation of a Modified Monoclonal Antibody (Anti-Daratumumab) Having Antigenic Specificity for Daratumumab (Target Immunoglobulin)

Provision of 500 µl of human anti daratumumab monoclonal antibody from the supplier (6 g/l in PBS solution)

A solution of 0.05 M of 1,2,4-benzenetricarboxylic anhydride was prepared in DMF The 500 µl of anti daratumumab monoclonal antibody solution was mixed with 10 µl of 1N sodium hydroxide and 50 µl of anhydride solution for 15 min at room temperature.

The reaction product was then dialyzed against phosphate buffer, 100 mM pH 7.4 for a night.

The dialyzed solution of modified anti daratumumab was then ready to use with improved IFE method.

Improved IFE method for mitigating daratumumab interference: Specific On-gel immunodisplacement of daratumumab with the sample spiked with daratumumab Improved IFE method was carried out on Hydrasys® electrophoresis system using current (unmodified) Immunofixation program and Hydragel 4 IF kit (Possibility of 4 samples per gel).

A membrane porous applicators where loaded in all wells with normal serum sample spiked with daratumumab 1 g/l was placed at position 6 of the applicator carrier adapted to Hydrasys® device.

Another comb placed at position 5 of applicator carrier where loaded with modified human anti daratumumab in wells number 10 and 13 aligned with tracks G and K of the gel The Hydrasys® immunofixation program was then started to allow all these combs to be simultaneously in contact with agarose immunofixation gel dedicated for 2 samples (21F) during 1 minute.

After application of samples and modified anti daratumumab on the gel, the migration started automatically and was carried out in less than 15 minutes at 20 W at 20° C.

During the migration, the modified anti daratumumab bounds and shifts out of gamma zone specifically daratumumab immunoglobulin in tracks G (track 10) and K (track 13) below which modified anti daratumumab where applied.

Each track of the gel was then incubated with a specific anti human antiserum (polyclonal antibody to specific immunoglobulin classes and types (IgG, IgA, IgM, IgK, IgL) following Hydragel Immunofixation process, by using specific Sebia Dynamic Mask or Standard Mask. Any type of applicator may be however used.

The gel was automatically stained with Acid Violet and distained before the final-stage drying.

FIG. 3C, IF result 1 is the classical IFE result of normal serum sample spiked with daratumumab where a monoclonal band is noticeable in tracks ELP, G and K.

FIG. 3C, IF result 2 is improved IFE result of the same normal sample spiked with daratumumab, where the monoclonal band was shifted with modified anti daratumumab out of gamma zone in tracks G and K, using the additional comb applied on the gel at position 6 of the carrier applicator; while signals appearing between alpha 1 and alpha 2 positions on tracks G and K are indicative of immune complex formed between daratumumab and modified anti daratumumab during migration step Example 2D See FIG. 3D, showing the possibility to resolve two interferents at the same time (within a single analysis), in the context of a monoclonal bi-therapy.

Example 2E

See FIG. 3E, showing the possibility to eliminate specifically one out of the two interferents contained in the assayed sample.

Example 3

Improved IFE method for analysis of a normal serum sample spiked with Bevacizumab (Creative Biolabs). Bevacizumab is a humanized monoclonal antibody (IgGK) involved in cancer, age related macular degeneration.

Preparation of a modified monoclonal antibody, based on the human anti-Bevacizumab monoclonal antibody (an anti-idiotype antibody from Creative Biolabs) was the same as for previous anti-idiotypes of Examples 1 and 2.

Improved IFE method for mitigating Bevacizumab interference was also carried out in the same way as with previous interfering monoclonal antibody drugs.

Results not shown, indicated the presence of Bevacizumab in ELP track and its displacement in tracks G and K when modified monoclonal anti human Bevacizumab was applied on the same tracks.

Example 4

Case of patients with oligoclonal gammopathy characterised by: Multiple weak bands of one or more types of heavy chains and by one or two types of light chains, with high polyclonal background.

Example 4A

Improved IFE method using modified anti IgK and modified ant IgL (modified with 1,2,4-benzenetricarboxylic anhydride), highly useful for interpretation in case of oligoclonal gammopathy with weak bands in high polyclonal background.

Preparation of modified polyclonal antibodies specific to human IgKappa and IgLambda (From Dako Denmark) with 1,2,4-benzenetricarboxylic anhydride.

Provision of 10 mL of polyclonal antibody specific to human Ig Kappa or 10 mL of polyclonal antibody specific to human Ig Lambda (10 g/L each, in phosphate buffer pH 7.4)

A 100 mM solution of 1,2,4-benzenetricarboxylic anhydride was prepared in Dioxolane The 10 mL of polyclonal antibody specific to human Ig Lambda or Ig Kappa was mixed with 300 µl of 5N sodium hydroxide and 2 mL of anhydride solution for 15 min at room temperature.

The reaction product was then dialyzed against phosphate buffer, 100 mM pH 7.4 for a night. The dialyzed solution of modified polyclonal anti human Ig Kappa or modified anti human Ig Lambda was then ready to use for on-gel immunodisplacement of Ig Kappa or Ig Lambda.

On-gel Immunodisplacement of IgK And IgL Followed by Immunofixation in Case of Oligoclonal Gammopathy (Sample C)

Two combs with porous membrane loaded with a known diluted oligoclonal sample (sample C) in all wells was placed at position 3 and 9 of the applicator carrier adapted to Hydrasys® device.

An additional comb with porous membrane loaded with modified antibody specific to Ig Kappa and modified antibody specific to Ig Lambda, respectively in well 3 (aligned with track G of upper row of the gel IF result 3, FIG. 4A) and well 10 (aligned with track G of upper row of the gel IF result 4, FIG. 4A) was placed at position 8 of the same applicator carrier.

The Hydrasys® immunofixation program was then started to allow all these combs to be simultaneously in contact with agarose immunofixation gel dedicated for 4 samples (4IF) during 1 minute.

After application of samples and modified antisera on the gel, the migration started automatically and was carried out in less than 15 minutes at 20 W at 20° C.

During the migration, the modified anti Ig Kappa and anti Ig Lambda bounds and shifts specifically Ig kappa and Ig Lambda in track G of samples deposited at position 9 of the applicator carrier (IF result 3 and 4 respectively).

Each track of the gel was then incubated with a specific anti human (polyclonal antibodies to specific immunoglobulin classes and types (IgG, IgA, IgM, IgK, IgL) following Hydragel Immunofixation process, by using specific Sebia Dynamic Mask or Standard Mask.

The gel was automatically stained with Acid Violet and distained before the final-stage drying.

FIG. 4A, IF result 1 and FIG. 4A, IF result 2 in the bottom row of the gel are repeated classical IFE results of sample C without immunodisplacement process.

FIG. 4A, IF result 3 is improved IFE result with IgK immunodisplacement of sample C using modified anti IgK on track G (G-IgK component), where one can now perceive a band on track G (band C1) that was hidden under the polyclonal background. This band is visible in G and L tracks, then interpreter would say GL.

FIG. 4A, IF result 4 is improved IFE result with IgL immunodisplacement of sample C using modified anti IgL on track G (G-IgL), where one can notice that the band designated as band C1 (in IF result 3) has disappear from G track (G-IgL), which is the confirmation that band C1 is GL.

In all cases, the band appearing in alpha 1 zone on track G is indicative of immune complex formed between modified anti Ig kappa and Ig Kappa or modified anti Ig Lambda and Ig Lambda, during migration step.

Example 4B

Improved IFE method using modified anti IgK and modified anti IgL (modified with pyromellitic dianhydride (1,2,4,5 benzene tetracarboxylic anhydre)), in case of oligoclonal gammopathy with weak bands in high polyclonal background observed in classical IFE.

Preparation of modified polyclonal antibodies specific to human IgKappa and IgLambda (from dako denmark) using a dianhydride, pyromellitic dianhydride (1,2,4,5 benzene tetracarboxylic anhydre).

Provision of 10 mL of polyclonal antibody specific to human Ig Kappa or 10 mL of polyclonal antibody specific to human Ig Lambda (10 g/L each phosphate buffer pH 7.4)

A solution of pyromellitic dianhydride 114 mM was prepared in Dioxolane

The 10 mL of polyclonal antibody specific to human Ig Lambda or Ig Kappa was mixed with 300 µL of 5N sodium hydroxide and 2 mL of anhydride solution for 15 min at room temperature.

The reaction product was then dialyzed against phosphate buffer, 100 mM pH 7.4 for a night.

The dialyzed solution of modified polyclonal anti human Ig Kappa or modified anti human Ig Lambda was then ready to use for on-gel immunodisplacement of Ig Kappa or Ig Lambda.

On-Gel Immunodisplacement of IgK and IgL Followed by Immunofixation in Case of Oligoclonal Gammopathy with High Polyclonal Background (Sample D)

Two combs with porous membrane loaded with a known diluted oligoclonal sample (sample D) in all wells was placed at position 3 and 9 of the applicator carrier adapted to Hydrasys® device. An additional comb with porous membrane loaded with modified antibody specific to Ig Kappa and modified antibody specific to Ig Lambda, respectively in well 3 (aligned with track G of upper row of the gel IF result 3, FIG. 4B) and well 10 (aligned with track G of upper row of the gel IF result 4, FIG. 4B) was placed at position 8 of the same applicator carrier.

The Hydrasys® immunofixation program was then started to allow all these combs to be simultaneously in contact with agarose immunofixation gel dedicated for 4 samples (4IF) during 1 minute.

After application of samples and modified antisera on the gel, the migration started automatically and was carried out in less than 15 minutes at 20 W at 20° C.

During the migration, the modified anti Ig Kappa and anti Ig Lambda bounds and shifts specifically Ig kappa and Ig Lambda in track G of samples deposited at position 9 of the applicator carrier (IF result 3 and 4 respectively in FIG. 4B).

Each track of the gel was then incubated with a specific anti human (polyclonal antibodies to specific immunoglobulin classes and types (IgG, IgA, IgM, IgK, IgL) following Hydragel Immunofixation process, by using specific Sebia Dynamic Mask or Standard Mask.

The gel was automatically stained with Acid Violet and distained before the final-stage drying.

FIG. 4B, IF result 1 and FIG. 4B, IF result 2 in the bottom row of the gel are repeated classical IFE results of sample D without any on-gel immunodisplacement process.

FIG. 4B, IF result 3 shows improved IFE result using modified anti IgK for specific displacement of IgK in track G, where one can now perceive a band on track G (band D 1) that was hidden under the polyclonal background. This band is now visible in G and L tracks, and then interpreter would say GL.

FIG. 4B, IF result 4 is improved IFE result IgL using modified anti IgL for displacement of IgL on track G (G-IgL), where one can notice that the band designated as band D1 (in IF result 3) has disappear from G track (G-IgL), which is the confirmation that band D1 is GL.

In all cases, the band appearing in alpha 1 zone on track G is indicative of immune complex formed between modified anti Ig kappa and Ig Kappa or modified anti Ig Lambda and Ig Lambda, during migration step.

Examples 4A and 4B

Interpretation

Another use of improved IFE method which is on-gel immunodisplacement of target protein in conjunction with immunofixation, is to help the interpreter to solve certain limitations of IFE more particularly when IFE give dubious results: case of patients with oligoclonal gammopathy characterised by: Multiple weak bands of one or more types of heavy chains and by one or two types of light chains, with high polyclonal background.

This circumstance is often difficult for the interpreter to give accurate information to the physician.

Since the staining of polyclonal background on each heavy chain track (G, A, M) is the addition of that of their corresponding light chain tracks (G=GK+G; A=AK+AL; M=MK+ML), a modified polyclonal antisera anti light chain (modified IgK or modified IgL) may be used as described previously (in the case therapeutic drugs) for specifically displace IgK or IgL components from heavy chain track (G or A or M).

For example, if multiples weak bands are underlying in a darker polyclonal background of G, K and L tracks, one can modify polyclonal antisera anti human light chain (IgK and IgL) with a carboxylic anhydride or carboxylic dianhydride for immunodisplacement of either IgL components or IgK components from G track in order to clarify the results on track G.

These immunodisplacements of IgK and IgL from track G are then followed by immunofixation using unmodified anti human antisera usually used in IFE method (anti human antisera IgG, IgA, IgM, IgK, IgL).

In that case, anti-human anti IgG is incubated with the gel on 3 different tracks of the sample: track G; track G-IgL=GK (G with IgL components displaced using modified anti human IgL); and track G-IgK=GL (G with IgK components displaced using modified anti human IgK).

Then by comparison of tracks G; G-IgL, G-IgK with tracks K and L, one can easily recognize bands belonging to G and K and bands belonging to G and L, thus help interpreter in bands identifications and classification.

Example 5

Figure 1A:
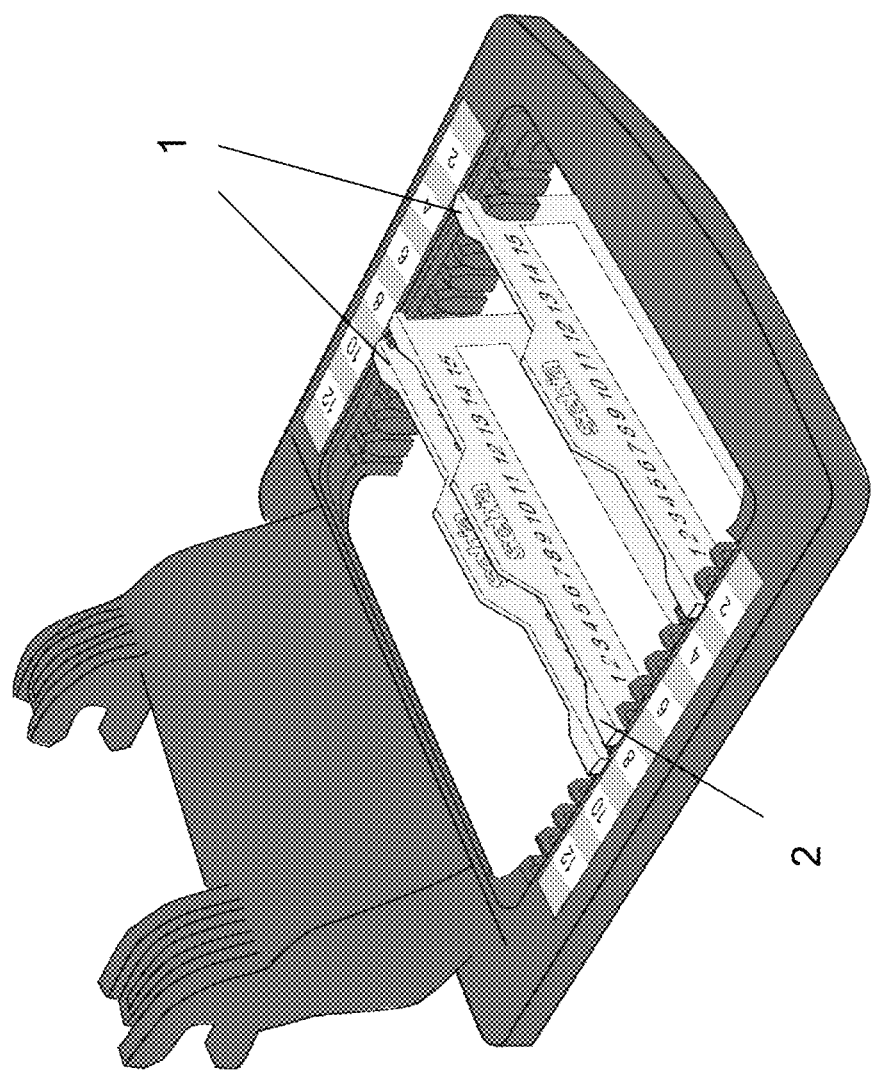
Figure 1B:
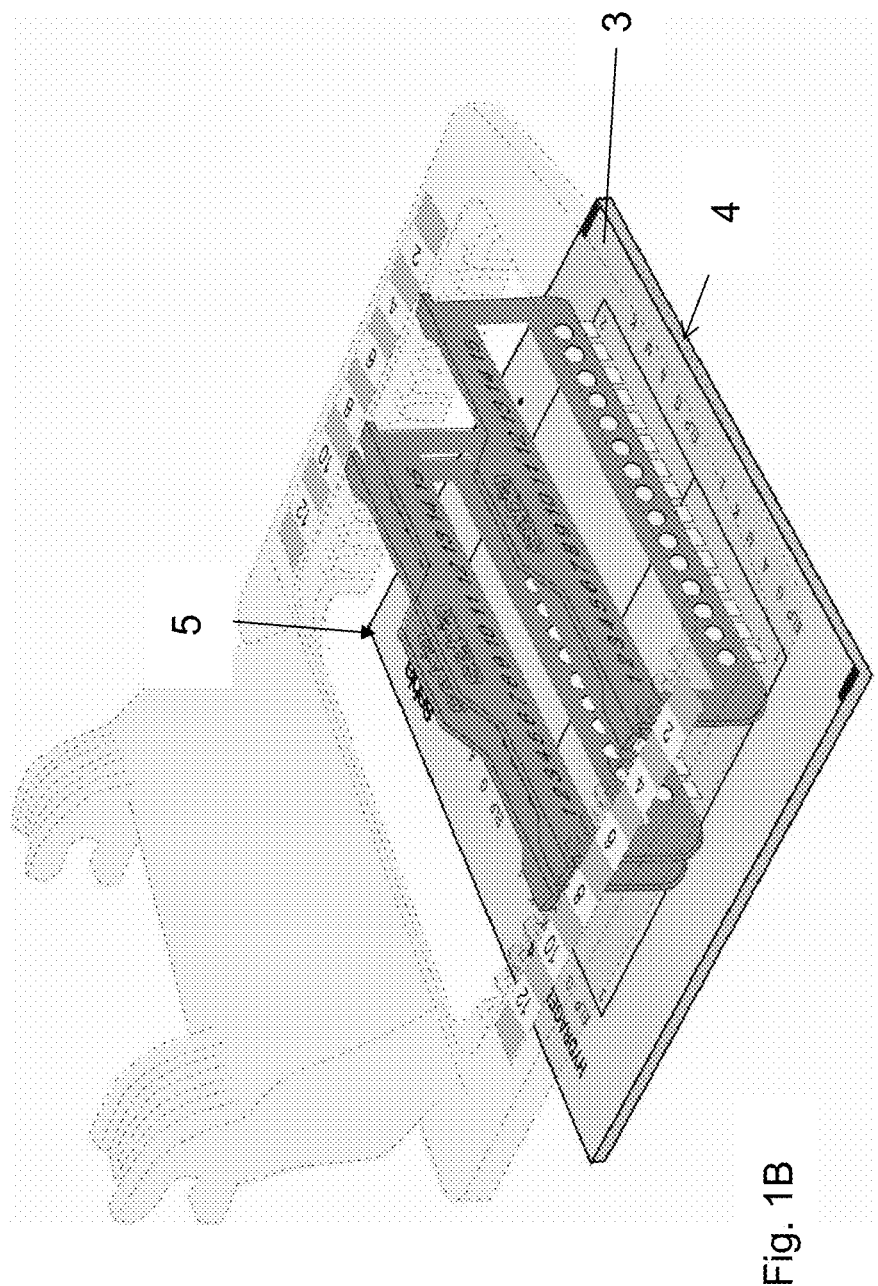
Figure 2:
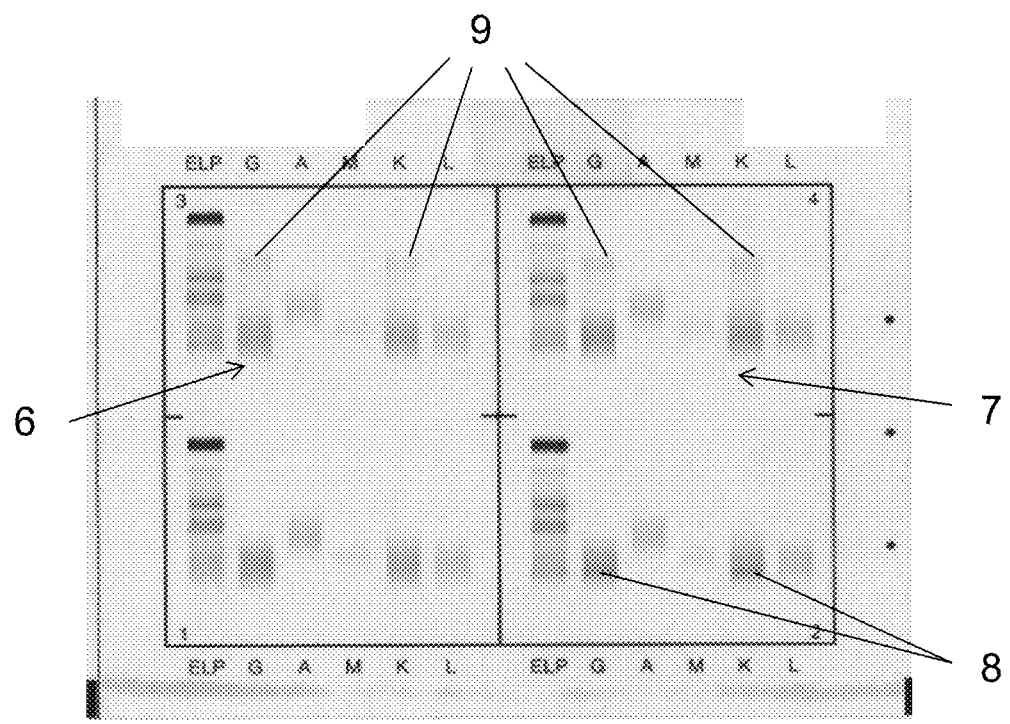
Figure 3A:
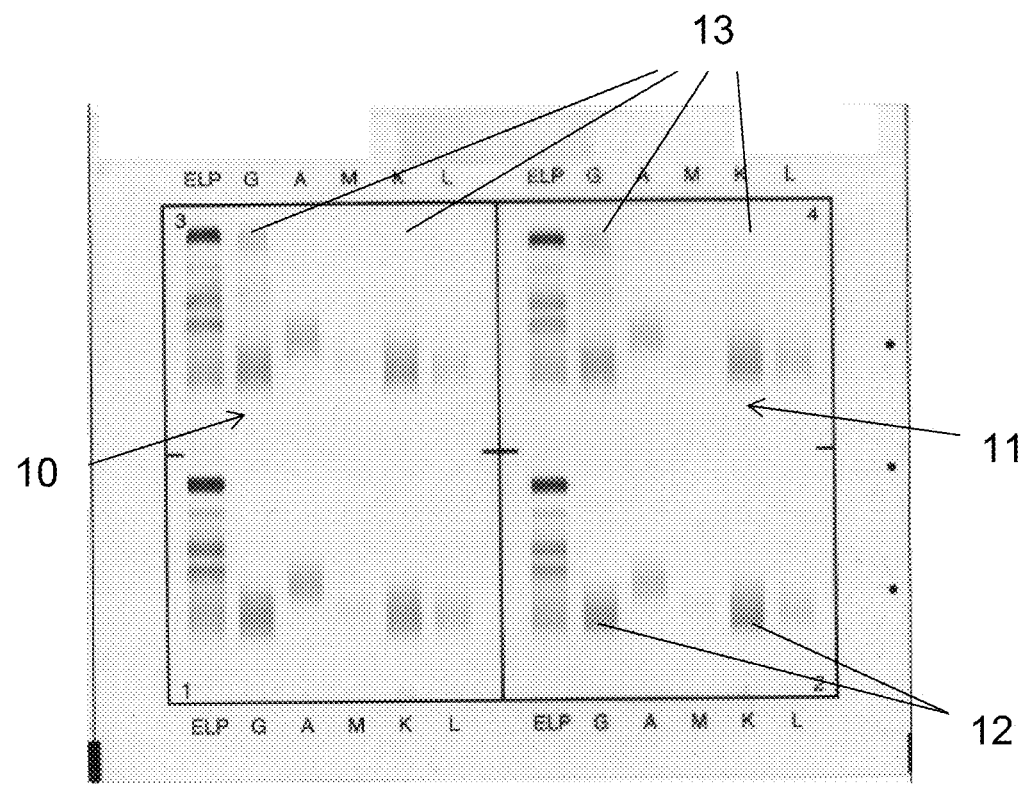
Figure 3B:
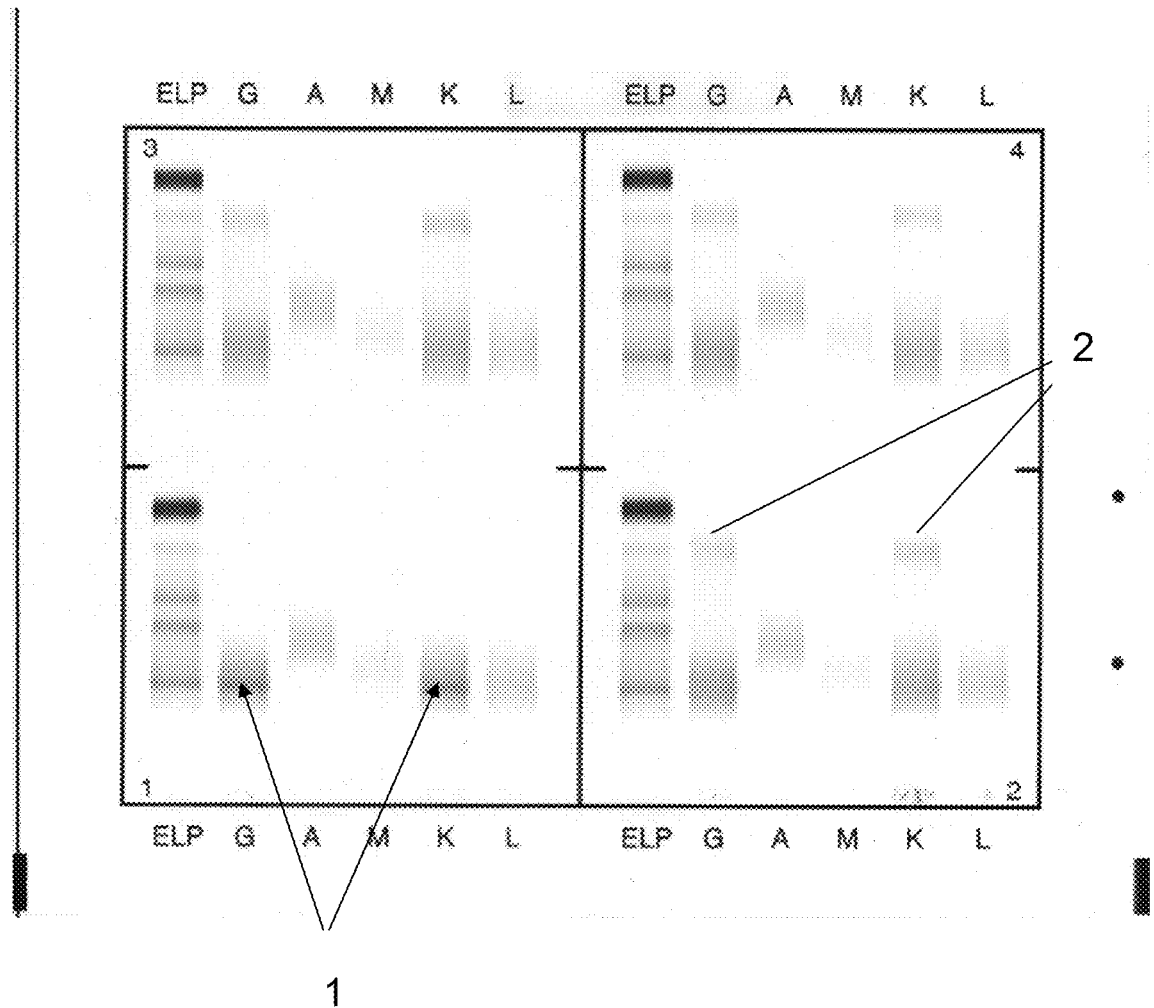
Figure 3C:
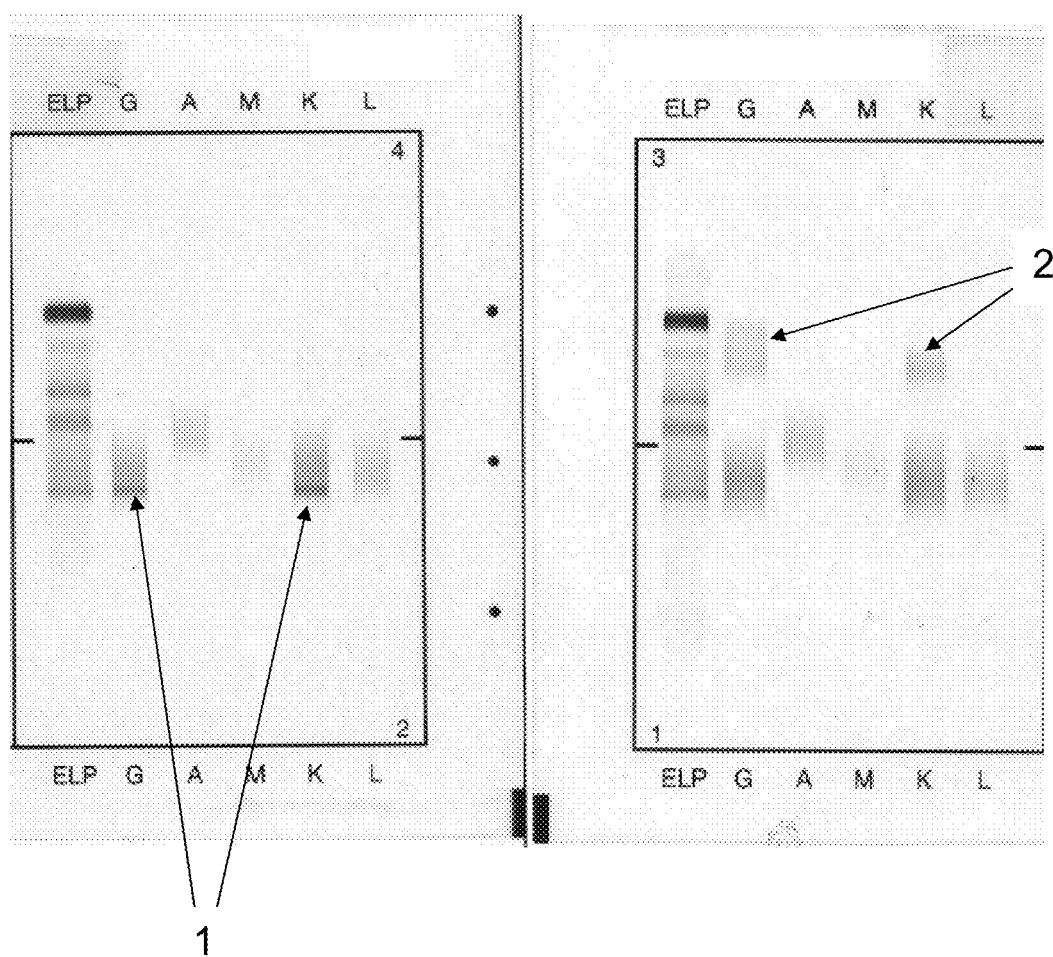
Figure 3D:
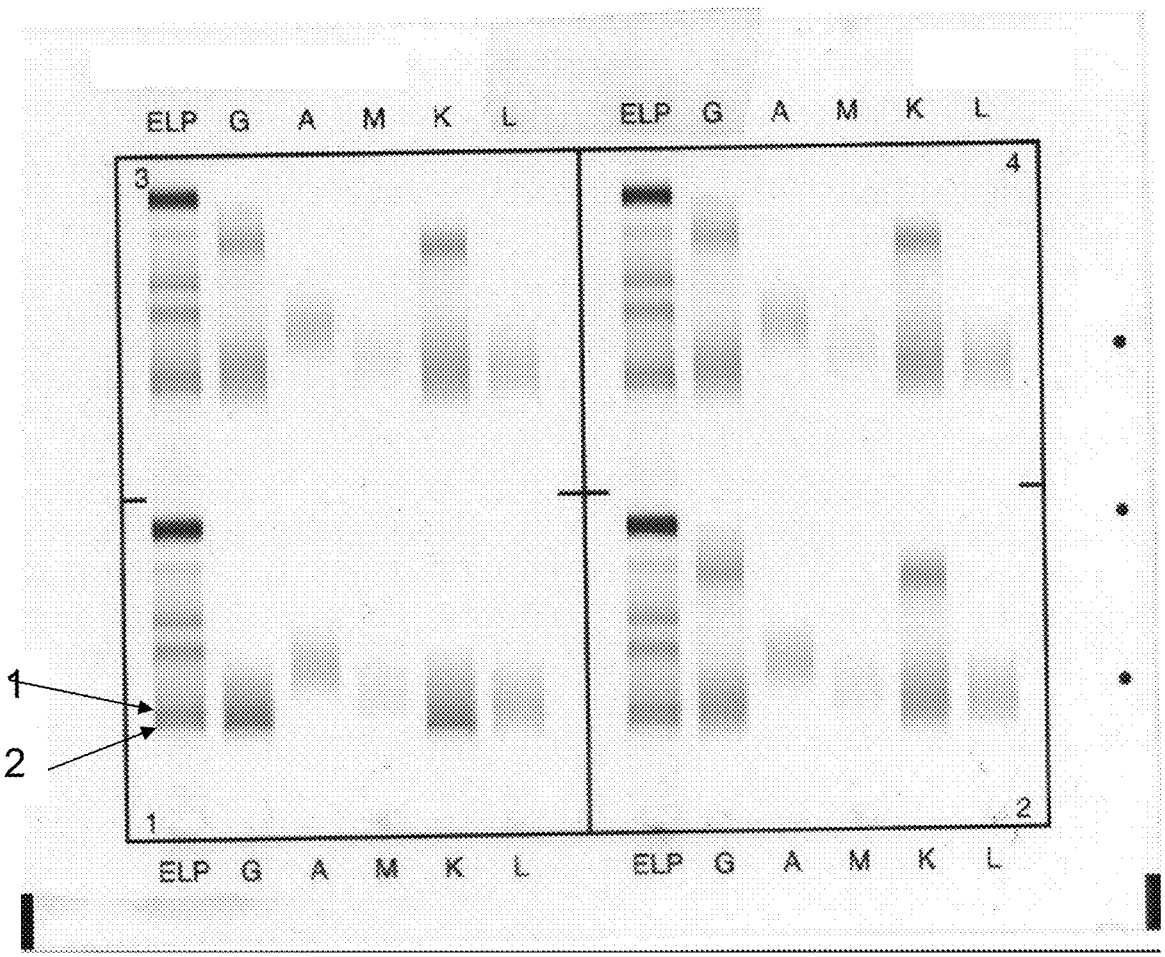
Figure 3E:
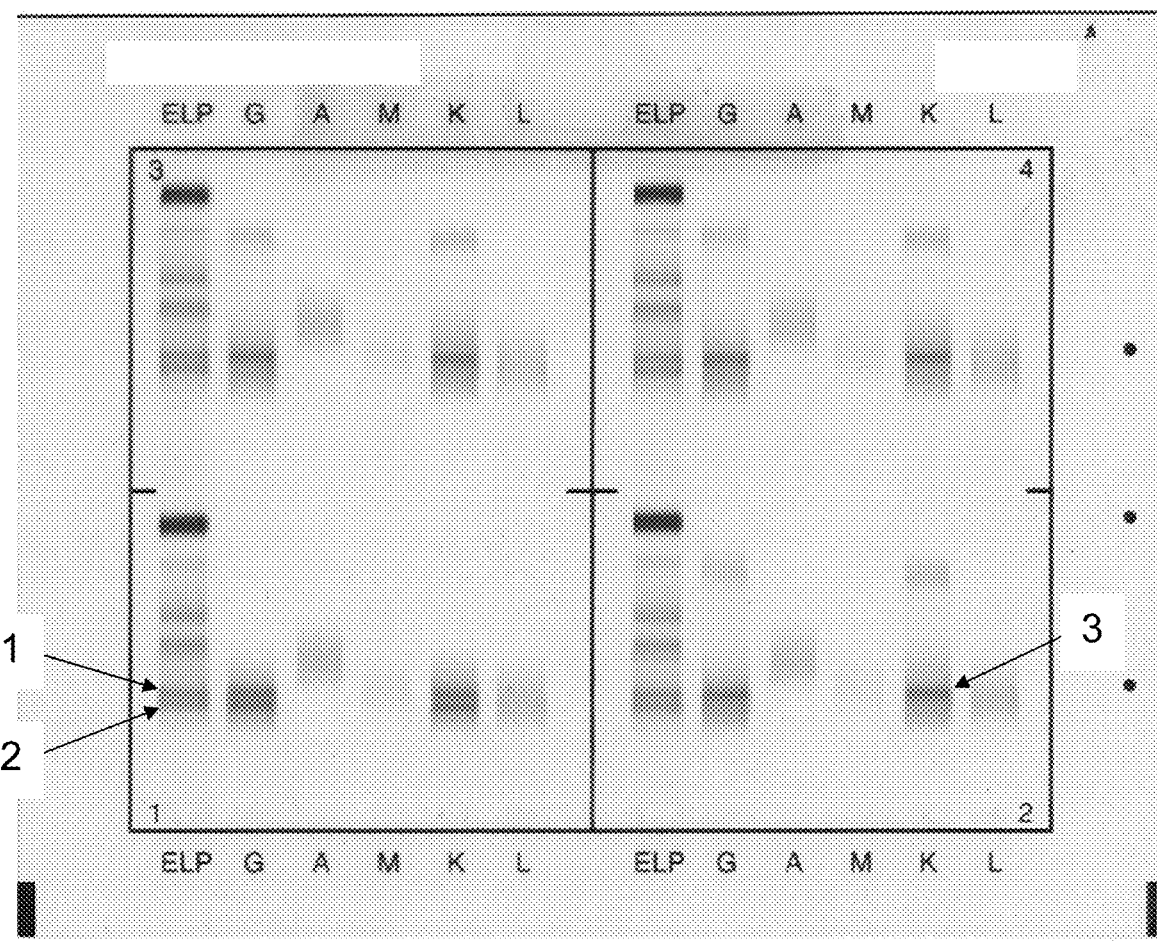
Figure 4A:
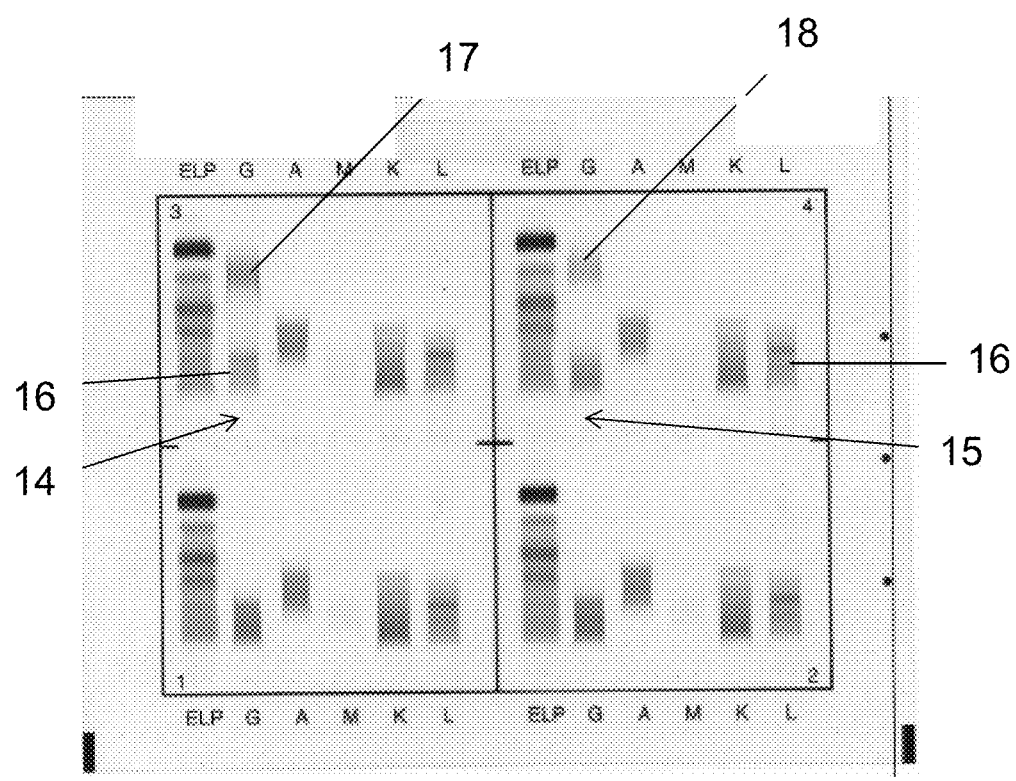
FIG. 4A shows on-gel immunodisplacement using modified anti IgK and modified anti IgL (with 1,2,4-benzenetricarboxylic anhydride) followed by immunofixation process in order to clarify IFE results of sample C characterized by multiple weak bands in a polyclonal background.
Figure 4B:
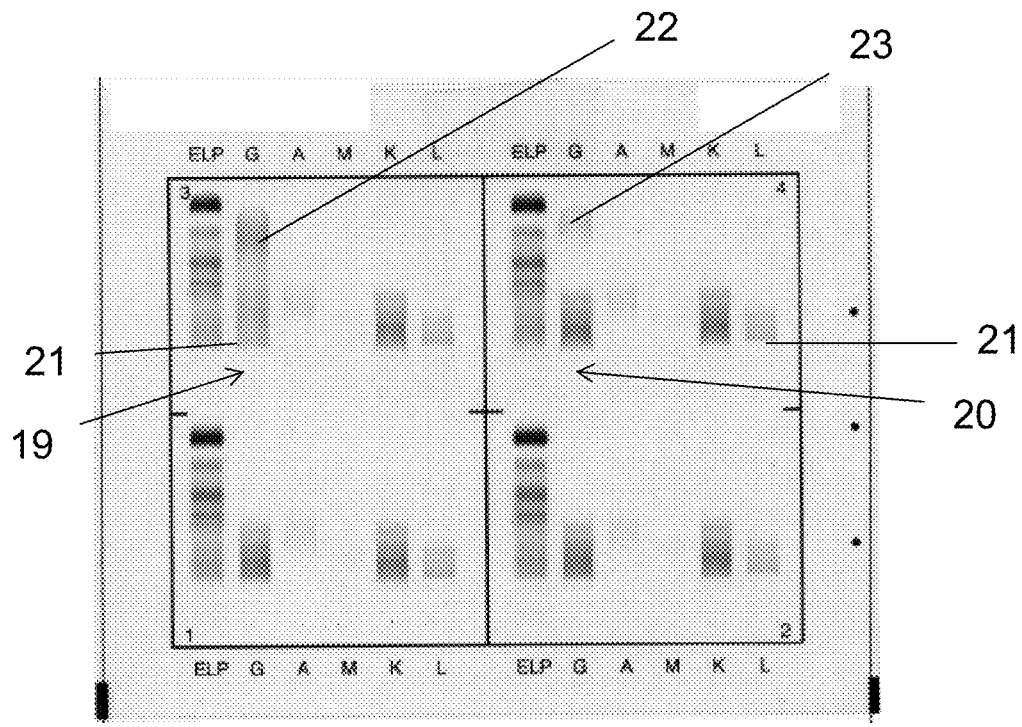
FIG. 4B is another example of on-gel immunodisplacement followed by IFE realized on sample D characterized by multiple weak bands present in the polyclonal background, where modified IgK and modified IgL were produced using pyromellitic dianhydride as chemical reagent.

Improved IFE method for resolving cases of IgA, IgD and IgE gammopathies without any corresponding light chain, which is typically (using common techniques in the art) an unresolved case known to those skilled in the art as "failure of immunofixation antisera", mimics Heavy-Chain disease (see (21), (22).

Preparation of modified polyclonal antibodies specific to human IgKappa and IgLambda (From Dako Denmark) with 1,2,4-benzenetricarboxylic anhydride used for resolving the cases of failure of anti light chain immunofixation reagent Provision of 10 mL of polyclonal antibody specific to human Ig Kappa or 10 mL of polyclonal antibody specific to human Ig Lambda (10 g/L each in phosphate buffer pH 7.4)

A 100 mM solution of 1,2,4-benzenetricarboxylic anhydride was prepared in Dioxolane The 10 mL of polyclonal antibody specific to human Ig Lambda or Ig Kappa was mixed with 300 µl of 5N sodium hydroxide and 2 mL of anhydride solution for 15 min at room temperature.

The reaction product was then dialyzed against phosphate buffer, 100 mM pH 7.4 for a night.

The dialyzed solution of modified polyclonal anti human Ig Kappa or modified anti human Ig Lambda was then ready to use.

Exempla 5 A

Cases of IgA Gammopathy Without Any Corresponding Light Chain on Classical Immunofixation in Serum Sample One comb with porous membrane loaded with diluted sample E in all wells was placed at position 3 of the applicator carrier adapted to Hydrasys® device.

A second comb loaded with diluted sample E from wells 9 to 14 was placed in position 9 of the applicator carrier adapted to Hydrasys® device.

A first additional comb with porous membrane loaded with modified antibody anti Ig Kappa in well 11 (aligned with track A in IF result 2, FIG. 5A) was placed in position 2 of the applicator carrier adapted to Hydrasys® device.

A second additional comb with porous membrane loaded with modified antibody anti Ig Lambda in well 11 (aligned with track A in IF result 4, FIG. 5A) was placed in position 8 of the applicator carrier adapted to Hydrasys® device.

The Hydrasys® immunofixation program was then started to allow all these combs to be simultaneously in contact with agarose immunofixation gel dedicated for 4 samples (4 IF) during 1 minute.

After application of samples and modified antisera on the gel, the migration started automatically and was carried out in less than 15 minutes at 20 W at 20° C.

Figure 5A:
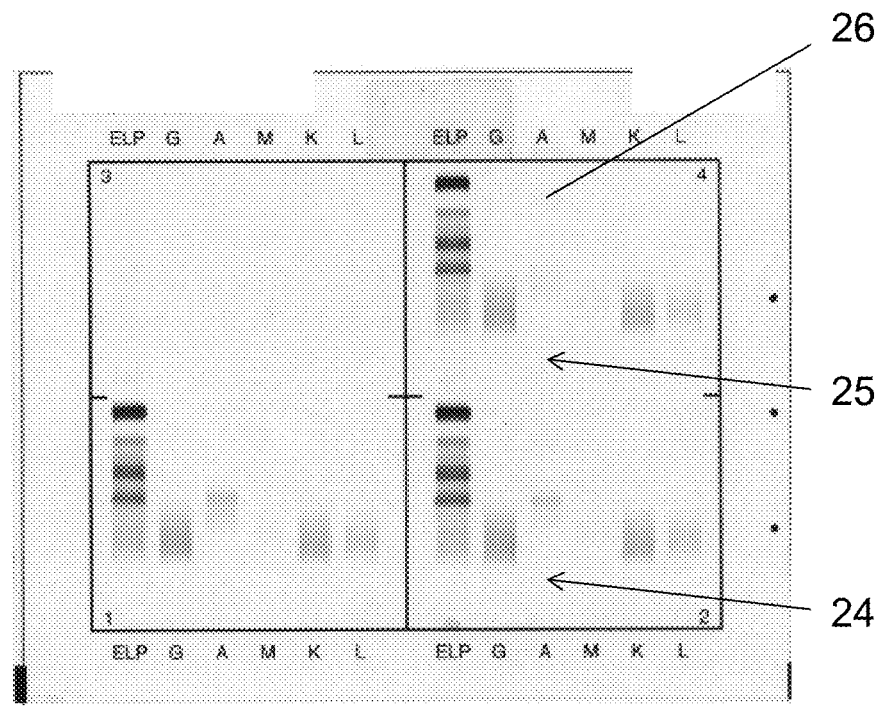

During the migration, the modified anti Ig Kappa (applied on position 2 of the applicator carrier) bounds and shifts specifically Ig kappa in track A of sample deposited in position 3 (IF result 2, FIG. 5A); and modified anti Ig Lambda (applied on position 8 of the applicator carrier) bounds and shifts specifically Ig Lambda in track A of sample deposited in position 9 (IF result 4, FIG. 5A)

Each track of the gel was then incubated with a specific anti human (polyclonal antibodies to specific immunoglobulin classes and types (IgG, IgA, IgM, IgK, IgL) following Hydragel Immunofixation process, by using specific Sebia Dynamic Mask or Standard Mask.

The gel was automatically stained with Acid Violet and distained before the final-stage drying.

FIG. 5A, IF result 1 shows classical IFE results of sample E that exhibited a band on track A without corresponding light chain (K or L).

FIG. 5A, IF result 2 shows improved IFE results of sample E after on-gel immunodisplacement of IgK on track A, using modified anti IgK (with 1,2,4-benzenetricarboxylic anhydride), where there is no reaction between the band on A track and modified anti IgK.

FIG. 5A, IF result 4 shows another improved IFE results of sample E after on-gel immunodisplacement of IgL on track A, using modified anti IgL (with 1,2,4-benzenetricarboxylic anhydride), where the band in A track is displaced with modified anti IgL. The reaction of modified anti IgL with this band in A track means that the corresponding light chain to IgA is IgL, then sample E is interpreted as AL.

Apart from the case of IgA heavy chain disease which is very rare, this situation often occur due to the quaternary structure of IgA molecule, where the epitopes for light chains can be sequestered by the folding of the molecule in the gel (Ref 1).

The inventors then thought that the access to the epitopes of light chain on IgA immunoglobulin molecule would be easier during electrophoresis, while IgA molecules are moving into the gel.

In these cases, the improved IFE using on-gel immunodisplacement of IgK and IgL from IgA using modified antiserum anti light chain (IgL and IgK) follow by immunofixation with capture anti IgA polyclonal antibody may be highly useful to clarify the IF results.

Exemple 5 B

Case of IgD Gammopathy Without any Corresponding Light Chain Visible on Classical Immunofixation in Serum Sample One comb with porous membrane loaded with diluted sample L in all wells was placed at position 6 of the applicator carrier adapted to Hydrasys® device.

An additional comb with porous membrane loaded with modified antibody anti Ig Kappa in well 13 and with modified antibody anti Ig Lambda in well 14 was placed in position 5 of the applicator carrier adapted to Hydrasys® device.

The Hydrasys® Bence Jones program was then started to allow all these combs to be simultaneously in contact with agarose Bence Jones gel dedicated for 2/4 samples (2/41F) during 5 minutes.

After application of samples and modified antisera on the gel, the migration started automatically and was carried out in less than 15 minutes at 20 W at 20° C.

During the migration, the modified anti Ig Kappa (applied on position 5 of the applicator carrier) bounds and shifts specifically Ig kappa of sample deposited in well 13 and modified anti Ig Lambda (applied on position 5 of the applicator carrier) bounds and shifts specifically Ig Lambda in of sample deposited in well 14

Tracks 10, 11, 12, 13 and 14 of the gel were then incubated respectively with a specific anti human polyclonal antibodies (capture antibody) anti IgD, anti IgK, anti IgL, anti IgD and anti IgD by using specific Sebia Dynamic Mask or Standard Mask.

The gel was automatically stained with Acid Violet and distained before the final-stage drying.

Figure 5B:
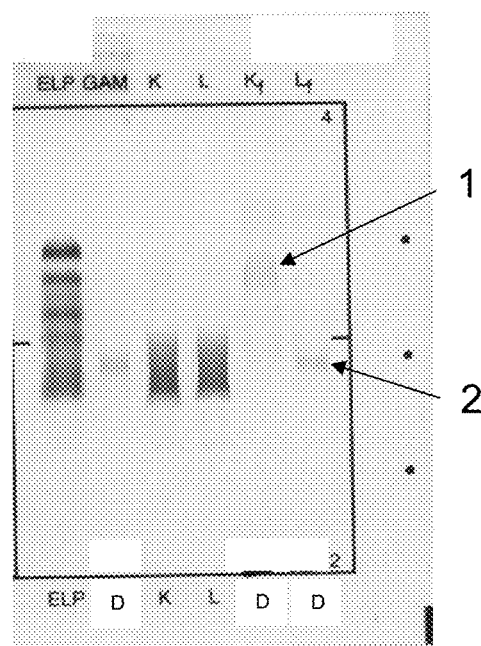

FIG. 5B, shows IFE results of sample L were IgD band do not react (or not visible) with capture anti IgK and ant IgL, but its displaced by modified anti IgK and revealed with capture antibody anti IgD. The reaction of modified anti IgK with IgD means that the corresponding light chain is IgK, then sample K is characterized as DK.

Apart from the case of IgD heavy chain disease which is very rare, this situation often occur due to the quaternary structure of IgD molecule, where the epitopes for light chains can be sequestered by the folding of the molecule in the gel.

The inventors then thought that the access to the epitopes of light chain on IgD immunoglobulin molecule would be easier during electrophoresis, while IgD molecules are moving into the gel.

In these cases, the improved IFE using on-gel immunodisplacement of IgK and IgL from IgD using modified antiserum anti light chain (IgL and IgK) followed by immunofixation with capture anti IgD polyclonal antibody may be highly useful to clarify the IF results.

Example 6

Improved IFE method for resolving cases of biclonal gammopathy where the bands are located at the same position on the electrophoresis pattern, and where one of the light chains is suspected to be a free light chain.

Procedure for modifying polyclonal antibodies specific to human IgG and IgLambda (From Dako Denmark) with 1,2,4-benzenetricarboxylic anhydride.

Provision of 10 mL of polyclonal antibody specific to human Ig G or 10 mL of polyclonal antibody specific to human Ig Lambda (10 g/L each in phosphate buffer pH 7.4)

A 100 mM solution of 1,2,4-benzenetricarboxylic anhydride was prepared in Dioxolane.

The 10 mL of polyclonal antibody specific to human Ig Lambda or Ig G was mixed with 300 µl of 5 N sodium hydroxide and 2 mL of anhydride solution for 15 min at room temperature.

The reaction product was then dialyzed against phosphate buffer, 100 mM pH 7.4 for a night.

The dialyzed solution of modified polyclonal anti human Ig G and modified anti human Ig Lambda was then ready to use for on-gel immunodisplacement in G track and L track.

Exemple 6A

Improved IFE method for resolving cases of biclonal gammopathy GK+GL where the two identical bands of heavy chain and two different bands of light chains are located at the same position on the electrophoresis pattern, and where one of the light chains (in track L) is suspected to be a free light chain. (Sample F)

Two combs with porous membrane loaded with a known diluted sample F in all wells was placed at position 3 and 9 of the applicator carrier adapted to Hydrasys® device.

An additional comb with porous membrane loaded with modified antibody specific to IgG in well 7 (aligned with track L of upper row of IF result 3, FIG. 6A) and modified antibody specific to Ig Lambda in well 10 (aligned with track G of upper row of the gel IF result 4, FIG. 6) was placed at position 8 of the same applicator carrier.

The Hydrasys® immunofixation program was then started to allow all these combs to be simultaneously in contact with agarose immunofixation gel dedicated for 4 samples (4 IF) during 1 minute.

After application of samples and modified antisera on the gel, the migration started automatically and was carried out in less than 15 minutes at 20 W at 20° C.

Figure 6A:
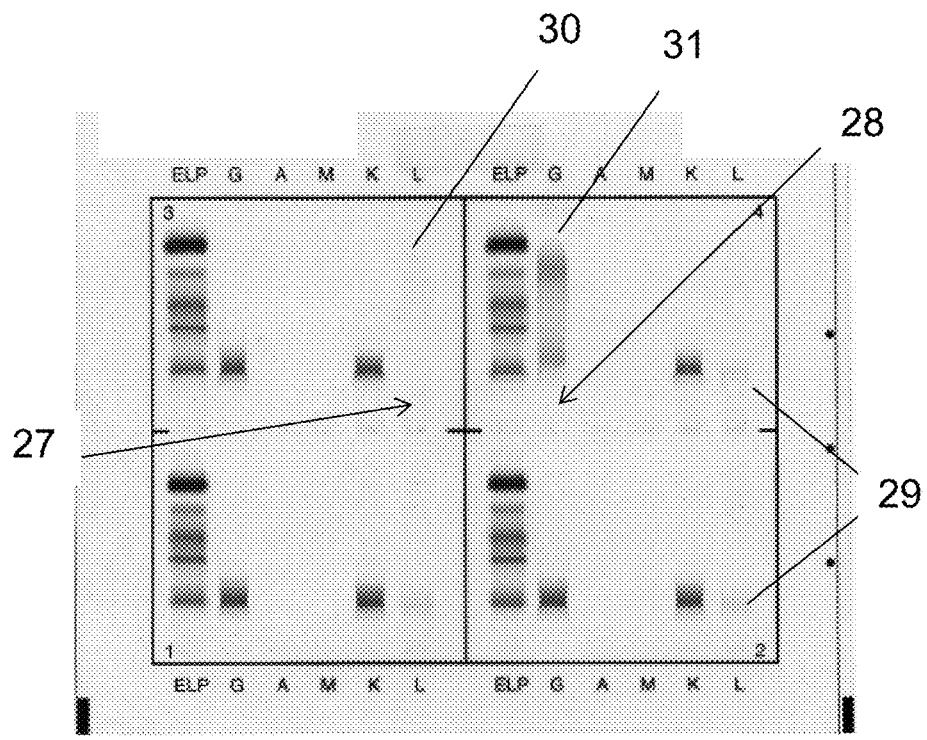

During the migration, the modified anti IgG bounds and shifts specifically IgL in track L of samples deposited at position 9 of the applicator carrier (FIG. 6A, IF result 3); while the modified anti IgL bounds and shifts specifically IgL in track G of samples deposited at position 9 of the applicator carrier (FIG. 6A, IF result 4).

Each track of the gel was then incubated with a specific anti human (polyclonal antibodies to specific immunoglobulin classes and types (IgG, IgA, IgM, IgK, IgL) following Hydragel Immunofixation process, by using specific Sebia Dynamic Mask or Standard Mask.

The gel was automatically stained with Acid Violet and distained before the final-stage drying. FIG. 6A, IF result 1 and result 2 show repeated IFE results of sample F that exhibited a light band on track L (band F1) co-migrating with the band on track G and track K. In this case, the interpreter will wonder if this band (F1) is GL or a free light chain lambda.

In FIG. 6A, IF result 3 shows another result IFE result with sample F, after on-gel immunodisplacement of IgL molecule on track L using modified anti IgG polyclonal. The displacement of band F1 on track L using modified anti IgG polyclonal is indicative of the presence of GL in this sample. Then sample F is characterized as GK and GL.

In FIG. 6A, IF result 4 shows another result IFE result with sample F, after on-gel immunodisplacement of IgL molecule on trackG using modified anti IgL polyclonal.

The displacement of band F1 on track L using modified anti IgG polyclonal is indicative of the presence of GL in this sample. Then sample G is characterized as GK and GL.

Another case of limitation of IFE where on-gel immunodisplacement of a target immunoglobulin or fragment thereof followed by immunofixation can be useful is the case of biclonal gammopathy, characterized by the presence of two identical bands of heavy chain and two different bands of light chains located at the same position on the electrophoresis pattern, and where one of the light chains can be suspected to be a free light chain.

In that case, improved IFE by on-gel immunodisplacement of suspected light chains bands (K or L) using modified antiserum anti heavy chains (with carboxylic anhydride or dianhydride), followed by immunofixation can be useful for removing the doubt in IFE results. In fact, if suspected band is a free light chain, it cannot react with modified antiserum anti heavy chains. If there is a reaction between the said band and on of the modified antiserum anti heavy chains (IgG, IgA, IgM), then the band in question is linked to this heavy chain, and is not a free light chain.

Exemple 6-B

Improved IFE method for resolving cases of biclonal gammopathy GK+MK where the two different bands of heavy chain and the identical band of light chains are located at the same position on the electrophoresis pattern, and where the M band is suspected to not have a corresponding light chain. (Sample G)

Preparation of modified polyclonal antibodies specific to human IgKappa and IgLambda (From Dako Denmark) with 1,2,4-benzenetricarboxylic anhydride was made as in exemple 5.

One comb with porous membrane loaded with a known diluted sample G in all wells was placed at position 3 and another comb loaded with diluted sample G in wells 2, 3, 4, 5, and 7 was placed at position 9 of the applicator carrier adapted to Hydrasys® device.

An additional comb with porous membrane loaded with modified antibody specific to IgK in well 12 (aligned with track M of bottom row of the gel) was placed at position 2 of the same applicator carrier. Another comb loaded with modified antibody specific to IgL in well 5 (aligned with track M of the upper row of the gel) was placed at position 8 of the applicator carrier.

The Hydrasys® immunofixation program was then started to allow all these combs to be simultaneously in contact with agarose immunofixation gel during 1 minute.

After application of samples and modified antisera on the gel, the migration started automatically and was carried out in less than 15 minutes at 20 W at 20° C.

Figure 6B:
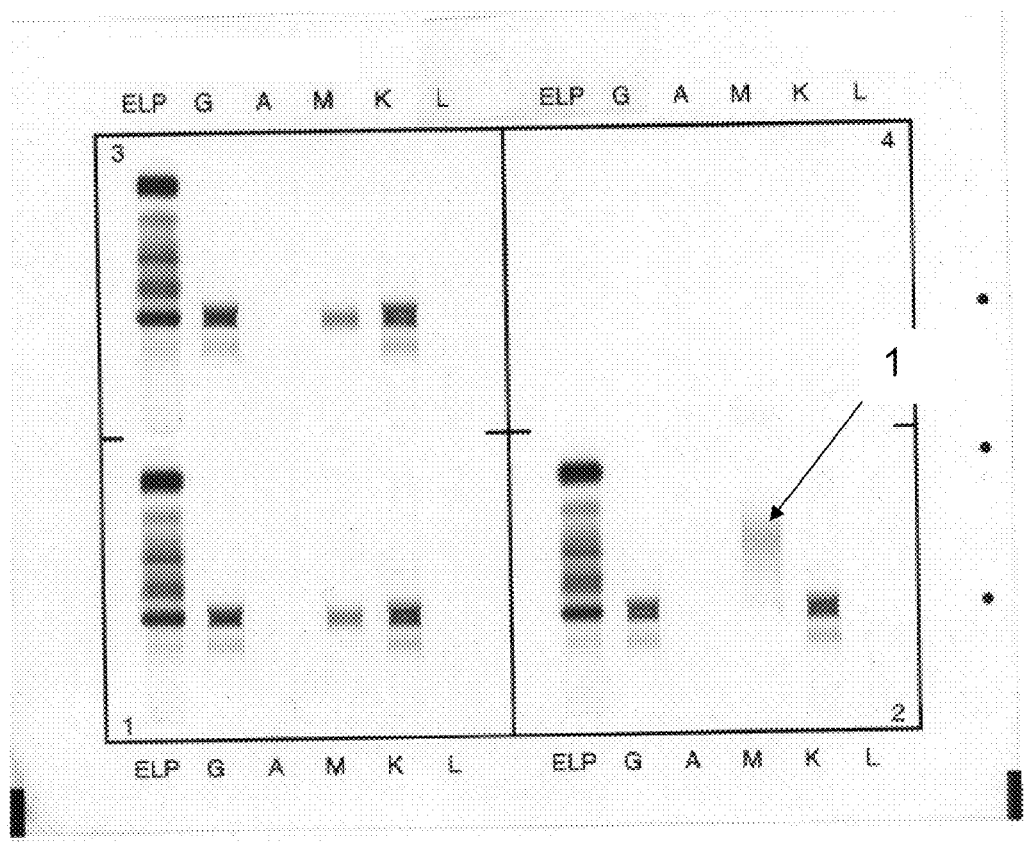
Figure 7:
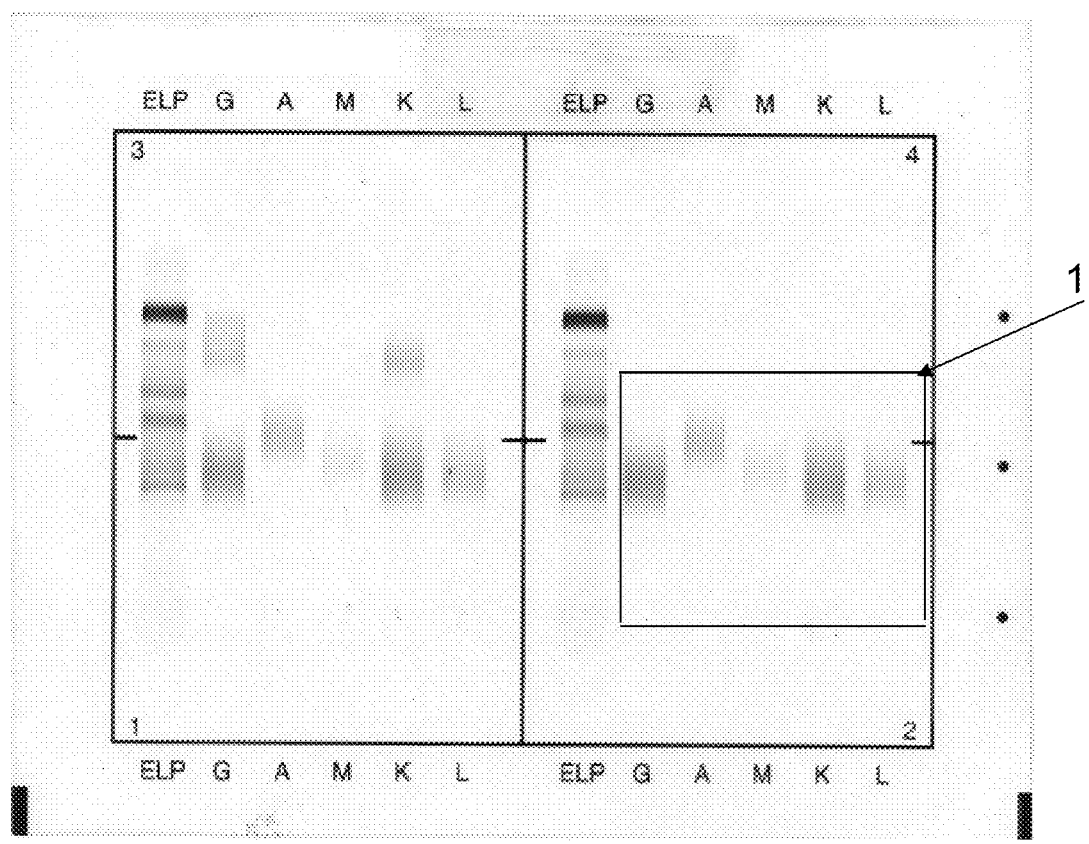

During the migration, the modified anti IgK bounds and shifts specifically IgK from track M of samples deposited at position 3 of the applicator carrier (FIG. 6-B, IF result 2); while the modified anti IgL bounds and shifts specifically IgL in track M of samples deposited at position 9 of the applicator carrier (FIG. 6-B, IF result 3).

Each track of the gel was then incubated with a specific anti human (polyclonal antibodies to specific immunoglobulin classes and types (IgG, IgA, IgM, IgK, IgL) following Hydragel Immunofixation process, by using specific Sebia Dynamic Mask or Standard Mask.

The gel was automatically stained with Acid Violet and distained before the final-stage drying.

FIG. 6-B, IF result 1 is the IFE result of sample G showing the co-migrating bands on tracks G, M and K. In this case, the interpreter will wonder if this IgM possess a corresponding light chain or not.

FIG. 6-B, IF result 2 shows improved IFE result of sample G, after on-gel immunodisplacement of IgK molecule on track M using modified anti IgK polyclonal. The displacement of M band with modified anti IgK polyclonal is indicative of the presence of MK in this sample. Then sample G is characterized as GK and MK.

FIG. 6-B, IF result 3 shows another improved IFE result with sample G, after on-gel immunodisplacement of IgL molecule on track M using modified anti IgL polyclonal, where there is no displacement of M band with modified anti IgL.

REFERENCES (1) Instruction Manual Sebia Ref 1201—release 2.2x 2015/03
(2) Reichert J M, Rosensweig C J, Faden L B, Dewitz M C. Monoclonal antibody successes in the clinic. Nat Biotechnol 2005; 23:1073-8.
(3) Rosman Z, Shoenfeld Y, Zandman-Goddard G. Biologic therapy for autoimmune diseases: an update. BMC Medicine 2013; 11:88.
(4) Kirkwood J M, Butterfield L H, Tarhini A A, Zarour H, Kalinski P, Ferrone S. Immunotherapy of cancer in 2012. CA Cancer J Clin 2012; 62:309-35.
(5) Reichert J M. Antibodies to watch in 2010. MAbs 2010; 2:84-100.
(6) Kubota T, Niwa R, Satoh M, Akinaga S, Shitara K, Hanai N. Engineered therapeutic antibodies with improved effector functions. Cancer Sci 2009; 100:1566-72.
(7) Carter P J. Potent antibody therapeutics by design. Nat Rev Immunol 2006; 6:343-57.
(8) Kola I, Landis J. Can the pharmaceutical industry reduce attrition rates? Nat Rev Drug Discov 2004; 3:711-5.
(9) Pavlou A K, Belsey M J. The therapeutic antibodies market to 2008. Eur J Pharm Biopharm 2005; 59:389-96.
(10) Durie B G, Harousseau J L, Miguel J S, Blade J, Barlogie B, Anderson K, et Al. International uniform response criteria for multiple myeloma. Leukemia 2006; 20:1467-1473.
(11) McCudden C R, Voorhees P M, Hainsworth S A, Whinna H C, Chapman J F, Hammett-Stabler C A, et al. Interference of monoclonal antibody therapies with serum protein electrophoresis tests. Clin Chem 2010; 56:1897-9.

(12) Kirkwood J M, Butterfield L H, Tarhini A A, Zarour H, Kalinski P, Ferrone S. Immunotherapy of cancer in 2012. CA Cancer J Clin 2012; 62:309-35.
(13) Janneke Ruinemans-Koerts, Cyriel Verkroost, Yvonne Schmidt-Hieltjes, Cees Wiegers, Joyce Curvers, Marc Thelen and Matthijs van Luin. Interference of therapeutic monoclonal immunoglobulins in the investigation of M-proteins Clin Chem Lab Med 2014; 52(11): 235-237.
(14) U.S. Pat. No. 5,567,282
(15) U.S. Pat. No. 8,609,435
(16) U.S. Pat. No. 8,859,211
(17) Alper C A and Johnson A M Vox. Sang. 17: 445 (1969),
(18) Cawley L P et al., Clin. Chem. 22: 1262 (1976),
(19) Ritchie R F and Smith R Clin. Chem. 22: 497, 1735, 1982 (1976).
(20) McCudden C et al., Clin Chem Lab Med 2016 June 1;54(6):1095-104, Monitoring multiple myeloma patients treated with daratumumab: teasing out monoclonal antibody interference.
(21) Su, L., Keren, D. F., & Warren, J. S. (1995). Failure of anti-lambda immunofixation reagent mimics alpha heavy-chain disease [2]. Clinical Chemistry, 41(1), 121-123.
(22) Cejka, J., Kithier, K. (1979). IgD Myeloma protein with "Unreactive" Light Chain Determinants. Clinical Chemistry, 25(8), 1495-1498.

The invention claimed is:

1. A method for immunofixation electrophoresis (IFE) analysis of a biological sample, comprising:
a) depositing at least one aliquot portion of the biological sample on a deposit area of an electrophoretic gel plate;
b) depositing on a second deposit area of the electrophoretic gel plate that is separated from the deposit area of step a),
which is on the same track as the track of the deposit area of step a), and
which is at a position between the cathodic extremity of the gel plate and the position of the sample deposit area of step a),
at least one antibody which is modified to bear additional negative electric charges, said modified antibody having antigenic specificity for a predetermined target immunoglobulin or fragment thereof present in the biological sample;
c) electrophoresis the gel plate to obtain a protein separation profile of the biological sample deposited in step a), so that during migration of the proteins the at least one modified antibody deposited in step b) binds specifically the predetermined target immunoglobulin or fragment thereof present in the biological sample, forming an immunocomplex, and shifts the immunocomplex to a position located outside the gamma zone of the electrophoretic track;
d) applying at least one capture antibody to the position of the electrophoretic track to which the immunocomplex has shifted, wherein said capture antibody has specificity for a particular antibody isotype, or has specificity for the target immunoglobulin or fragment thereof, or has specificity for a particular antibody isotype and/or target immunoglobulin or fragment thereof as found in the immunocomplex between the target immunoglobulin or fragment thereof and the at least one modified antibody, thereby permitting immunofixation by the precipitation of immunocomplexes outside the gamma zone of the immunoglobulin in the electrophoretic track,
wherein the method does not include pre-incubation of the sample with the modified antibody prior to deposition of the sample on the gel, such that the sample and the modified antibody can interact with each other only after both their deposition on the gel and application of an electric field; and
e) staining the immunocomplexes formed in step d).

2. The method of claim 1, in which several aliquot portions of the biological sample are deposited on parallel tracks of the gel plate in step a), with at least one track being loaded with at least one modified antibody according to step b).

3. The method of claim 2, in which at least one track on the gel plate is a reference track which is not deposited with at least one capture antibody as in step d), but is instead contacted with a fixative solution, steps a) to c) remaining the same.

4. The method of claim 1, wherein six aliquot portions of the biological sample are deposited on parallel tracks of the gel plate in step a), including a reference track and five tracks that are respectively contacted in step d) with capture antibodies specific to IgG, IgA, IgM, IgK and IgL, with at least one track being loaded with at least one modified antibody according to step b).

5. The method of claim 1, further comprising a step of comparing the electrophoretic profile(s) obtained by performing the steps a) to d) with electrophoretic profile(s) obtained in the same conditions and with the same biological sample, but in the absence of any modified antibody as defined in step b).

6. The method of claim 5, in which the predetermined target immunoglobulin or fragment thereof is a therapeutic monoclonal antibody selected from the group consisting of Adalimumab, Trastuzumab, Ofatumumab, Siltuximab, Rituximab, Bevacizumab, Infliximab, Cetuximab, Efalizumab Natalizumab, Panitumumab, Tolicizumab, Clenoliximab, Etaracizumab, Visilizumab, Elotuzumab, Nimotuzumab, Ramicirumab, Elotuzumab, Daratumumab, Mapatumumab, Golimumab, Ustekinumab, Nivolumab, fragments thereof, functionally equivalent antibodies thereof and mixtures thereof.

7. The method of claim 5, in which the predetermined target immunoglobulin or fragment thereof is a monoclonal immunoglobulin or fragment thereof selected from the group consisting of IgG, IgA, IgM, IgD, IgE, kappa chain, lambda chain, free kappa chain and free lambda chain, or a polyclonal serum having an isotype selected from the group consisting of IgG, IgA, IgM, IgD, IgE, kappa chain, lambda chain, free kappa chain and free lambda chain.

8. The method of claim 1, in which the predetermined target immunoglobulin or fragment thereof is selected from the group consisting of a therapeutic monoclonal antibody or a fragment thereof, an endogeneous monoclonal immunoglobulin or a fragment thereof, an endogeneous polyclonal antiserum, and mixtures thereof.

9. The method of claim 1, in which the antibody that is modified is a human or animal monoclonal antibody, or a human or animal polyclonal antiserum, which is specific for an immunoglobulin pertaining to an isotypic class selected from the group consisting of IgG, IgA, IgM, IgD and IgE, or specific for an immunoglobulin pertaining to an isotypic type selected from the group consisting of kappa and lambda, or specific for a free light chain selected from the group consisting of free kappa and free lambda.

10. The method of claim 9, in which, using two distinct modified antibodies, both the kappa and/or lambda components of a particular immunoglobulin isotype are displaced within a single gel experiment.

11. The method of claim 1, in which the ratio of the concentration of modified antibody specific for the predetermined target immunoglobulin or fragment thereof to the concentration of the predetermined target immunoglobulin or fragment thereof in the analyzed sample is from 0.1/1 to 20/1.

12. The method of claim 1, in which the modified antibody is a reaction product of an antibody with a carboxylic acid anhydride.

13. The method of claim 12, wherein the carboxylic acid anhydride is an acid anhydride that is 1,2,4-benzenetricarboxylic anhydride or a dianhydride selected from the group consisting of pyromellitic dianhydride (1,2,4,5 benzene tetracarboxylic anhydre), benzophenone-3,3',4,4'-tetracarboxylic dianhydride, and diethylenetriaminepentaacetic dianhydride.

14. The method according to claim 1, wherein the modified antibody is obtained by:
providing an antibody solution in a concentration from 0.1 to 30 g/L, and
adding to said antibody solution a carboxylic acid anhydride dissolved in a suitable anhydrous solvent selected from the group consisting of dioxolane, dimethylformamide and dimethylsulfoxide, the addition being performed at a pH from 7.5 to 9, and
recovering the obtained modified antibody.

15. The method of claim 14, wherein the carboxylic acid anhydride is added at a concentration from 10 mM to 200 mM or from 50 to 160 mM.

16. The method of claim 1, wherein the deposit area of the at least one modified antibody is at a distance from the deposit area of the biological sample that is equal to or less than 5 millimeters.

17. The method of claim 16, wherein the deposit area of the at least one modified antibody is at a distance from the deposit area of the biological sample that is from 2 to 3 millimeters.

18. The method of claim 1, wherein the biological sample is selected from the group consisting of serum, urine and cerebrospinal fluid sample.

19. The method according to claim 1, which further comprises a step of analyzing and/or interpreting the IFE results and/or concluding about the health status of the patient, the biological sample of which has been subjected to the method.

20. A method for detection of interfering immunoglobulin(s) or fragment(s) thereof suspected to be present in the biological sample of a patient comprising the step of performing a method for immunofixation electrophoresis (IFE) analysis according to claim 1 on a sample drawn from said patient, wherein the predetermined target immunoglobulin(s) or fragment(s) thereof targeted in said IFE method is (are) said suspected interfering immunoglobulin(s) or fragment(s) thereof.

21. The method of claim 1, wherein in step c) the binding of the at least one modified antibody and the predetermined target immunoglobulin or fragment thereof occurs when the migration path of the at least one modified antibody crosses the migration path of the predetermined target immunoglobulin or fragment thereof.

22. The method of claim 21, wherein in step c) the immunocomplex is shifted to enable its immunoprecipitation at a position located outside a gamma zone of the immunoglobulin in the electrophoretic track.

23. The method of claim 1, wherein in step c) the immunocomplex is shifted to enable its immunoprecipitation at a position located outside a gamma zone of the immunoglobulin in the electrophoretic track.

24. The method of claim 1, wherein the electrophoretic gel plate is made of an agarose gel.

25. The method of claim 24, wherein the gel has a concentration of agarose from 0.5% to 2%, in particular 0.8%.

26. The method of claim 24, wherein the electrophoretic gel plate is surrounded by a buffer that is a Tris/Veronal buffer at pH 9.2 when the immunofixation electrophoresis method is carried out.

27. The method of claim 24, wherein the immunocomplex that is shifted is a soluble immunocomplex that does not precipitate or is not found in a precipitated form in the gel unless it is complexed with at least one capture antibody.

28. The method of claim 1, wherein the step e) of staining the immunocomplexes is carried out with a reagent selected from amido black, acid violet, and coomassie red reagent.

29. The method of claim 1, wherein the at least one antibody which is modified to bear additional negative electric charges and has antigenic specificity for a predetermined target immunoglobulin or fragment thereof present in the biological sample has an electrophoretic mobility ($\mu ep$) increased by a ratio between 2 and 6 over the electrophoretic mobility ($\mu ep$) of the same antibody that is non-modified, the $\mu ep$ being determined by capillary electrophoresis in free solution and expressed in cm2/V.

* * * * *